United States Patent
Jung et al.

(10) Patent No.: US 11,767,315 B2
(45) Date of Patent: Sep. 26, 2023

(54) HETEROCYCLIC COMPOUND AND ORGANIC LIGHT-EMITTING DEVICE INCLUDING SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 589 days.

(21) Appl. No.: 16/967,201

(22) PCT Filed: Jun. 14, 2019

(86) PCT No.: PCT/KR2019/007198
§ 371 (c)(1),
(2) Date: Aug. 4, 2020

(87) PCT Pub. No.: WO2019/240532
PCT Pub. Date: Dec. 19, 2019

(65) Prior Publication Data
US 2021/0047306 A1 Feb. 18, 2021

(30) Foreign Application Priority Data
Jun. 14, 2018 (KR) .................. 10-2018-0068054

(51) Int. Cl.
*C07D 405/14* (2006.01)
*C07D 405/04* (2006.01)
(Continued)

(52) U.S. Cl.
CPC ......... *C07D 405/14* (2013.01); *C07D 405/04* (2013.01); *C07D 405/10* (2013.01);
(Continued)

(58) Field of Classification Search
CPC ............. H10K 85/654; H10K 85/6574; H10K 85/6576
See application file for complete search history.

(56) References Cited

U.S. PATENT DOCUMENTS

| 9,406,892 B2 | 8/2016 | Zeng et al. |
| 10,622,565 B2 | 4/2020 | Parham et al. |

(Continued)

FOREIGN PATENT DOCUMENTS

| CN | 107428701 A | 12/2017 |
| JP | 2016-128432 | 7/2016 |

(Continued)

*Primary Examiner* — Vu A Nguyen
(74) *Attorney, Agent, or Firm* — Bryan Cave Leighton Paisner LLP

(57) ABSTRACT

Provided is a heterocyclic compound of Chemical Formula 1:

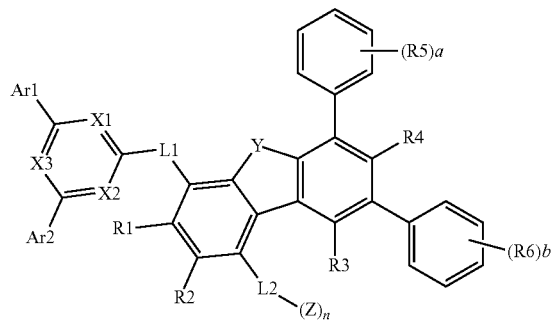

wherein:
X1 to X3 are each independently is N or CH;
at least two of X1 to X3 are N;
Y is O or S;

(Continued)

R1 to R6 each independently is hydrogen, deuterium, a halogen group, a nitrile group, or a substituted or unsubstituted: alkyl, silyl, aryl or heteroaryl group;

Ar1 and Ar2 each independently is a substituted or unsubstituted aryl or heteroaryl group;

L1 and L2 each independently is a direct bond, or a substituted or unsubstituted arylene or heteroarylene group;

Z is a nitrile group, a halogen group, or a substituted or unsubstituted: alkyl, silyl, aryl or heteroaryl group;

n is an integer of 0 to 2; and a and b are an integer of 0 to 5, and an organic light-emitting device including the same.

6 Claims, 1 Drawing Sheet

(51) Int. Cl.
*C07D 405/10* (2006.01)
*C07D 409/14* (2006.01)
*H01L 51/00* (2006.01)
*H01L 51/50* (2006.01)
*H10K 85/60* (2023.01)

(52) U.S. Cl.
CPC ......... *C07D 409/14* (2013.01); *H10K 85/615* (2023.02); *H10K 85/654* (2023.02); *H10K 85/6574* (2023.02); *H10K 85/6576* (2023.02)

(56) References Cited

U.S. PATENT DOCUMENTS

| | | | |
|---|---|---|---|
| 11,208,402 B2* | 12/2021 | Jung | C07D 409/14 |
| 2016/0028021 A1* | 1/2016 | Zeng | H10K 85/6576 |
| | | | 252/301.16 |
| 2016/0093808 A1* | 3/2016 | Adamovich | H10K 85/657 |
| | | | 252/301.16 |
| 2016/0197285 A1* | 7/2016 | Zeng | H10K 85/6574 |
| | | | 544/216 |
| 2016/0226001 A1 | 8/2016 | Parham et al. | |
| 2017/0025618 A1* | 1/2017 | Zheng | H10K 85/6572 |
| 2017/0054087 A1* | 2/2017 | Zeng | H10K 85/6576 |
| 2018/0037546 A1* | 2/2018 | Sugino | C07D 405/14 |
| 2018/0051007 A1 | 2/2018 | Jung et al. | |
| 2018/0301639 A1* | 10/2018 | Zeng | C07D 487/04 |
| 2019/0047991 A1 | 2/2019 | Jung et al. | |

FOREIGN PATENT DOCUMENTS

| | | |
|---|---|---|
| KR | 10-2016-0028524 | 3/2016 |
| KR | 10-2016-0054582 | 5/2016 |
| KR | 10-2018-0051355 | 5/2018 |

* cited by examiner

【FIG. 1】
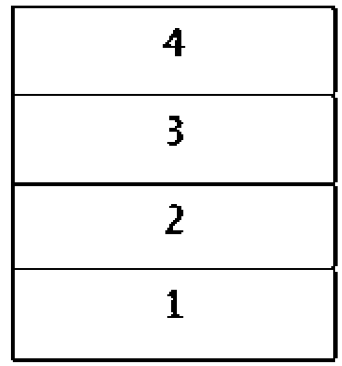
【FIG. 2】
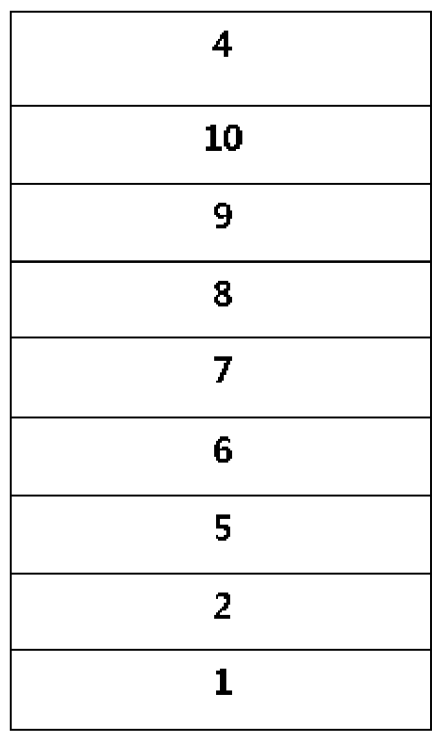

HETEROCYCLIC COMPOUND AND ORGANIC LIGHT-EMITTING DEVICE INCLUDING SAME

CROSS-REFERENCE TO RELATED APPLICATION(S)

This application is a National Stage Application of International Application No. PCT/KR2019/007198 filed on Jun. 14, 2019, which claims priority to and the benefits of Korean Patent Application No. 10-2018-0068054, filed with the Korean Intellectual Property Office on Jun. 14, 2018, the entire contents of which are incorporated herein by reference.

TECHNICAL FIELD

The present specification relates to a heterocyclic compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a heterocyclic compound, and an organic light emitting device including the same.

Technical Solution

One embodiment of the present specification provides a heterocyclic compound of Chemical Formula 1:

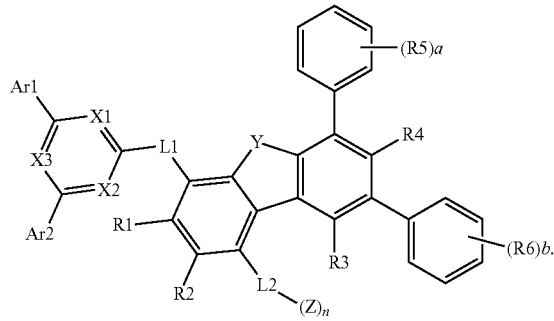

Chemical Formula 1

In Chemical Formula 1:
X1 to X3 are the same as or different from each other, and each independently is N or CH;
at least two or more of X1 to X3 are N;
Y is O or S;
R1 to R6 are the same as or different from each other, and each independently is hydrogen, deuterium, a halogen group, a nitrile group, a substituted or unsubstituted alkyl group, a substituted or unsubstituted silyl group, a substituted or unsubstituted aryl group, or a substituted or unsubstituted heteroaryl group;
Ar1 and Ar2 are the same as or different from each other, and each independently is a substituted or unsubstituted aryl group, or a substituted or unsubstituted heteroaryl group;
L1 and L2 are the same as or different from each other, and each independently is a direct bond, a substituted or unsubstituted arylene group, or a substituted or unsubstituted heteroarylene group;
Z is a nitrile group, a halogen group, a substituted or unsubstituted alkyl group, a substituted or unsubstituted silyl group, a substituted or unsubstituted aryl group, or a substituted or unsubstituted heteroaryl group;
n is an integer of 0 to 2;
when n is 0, hydrogen bonds to L2;
when n is 2, the Zs are the same as or different from each other, and
a and b are an integer of 0 to 5, and when a and b are a plural number, the substituents in the parentheses are the same as or different from each other.

Another embodiment of the present specification provides an organic light emitting device including a first electrode; a second electrode provided opposite to the first electrode; and one, two or more organic material layers provided between the first electrode and the second electrode, wherein one or more layers of the organic material layers include the heterocyclic compound.

Advantageous Effects

A heterocyclic compound according to one embodiment of the present specification can be used as a material of an organic material layer of an organic light emitting device, and by using the same, efficiency can be enhanced, a low driving voltage can be obtained, and/or lifetime properties can be enhanced in the organic light emitting device.

DESCRIPTION OF THE DRAWINGS

FIG. 1 illustrates an organic light emitting device according to one embodiment of the present specification.

FIG. 2 illustrates an organic light emitting device according to one embodiment of the present specification.

REFERENCE NUMERALS

1: Substrate
2: First Electrode
3: Organic Material Layer
4: Second Electrode
5: Hole Injection Layer
6: Hole Transfer Layer
7: Electron Blocking Layer
8: Light Emitting Layer
9: Electron Transfer Layer
10: Electron Injection Layer

DETAILED DESCRIPTION

Hereinafter, the present specification will be described in more detail.

One embodiment of the present specification provides a heterocyclic compound of Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a nitrile group, a substituted or unsubstituted alkyl group, a substituted or unsubstituted cycloalkyl group, a substituted or unsubstituted silyl group, a substituted or unsubstituted aryl group, and a substituted or unsubstituted heterocyclic group, or being substituted with a substituent linking two or more substituents among the substituents illustrated above, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group, and the like.

In the present specification, examples of the halogen group can include fluorine, chlorine, bromine or iodine.

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, iso-pentyl, neopentyl, tert-pentyl, hexyl, n-hexyl, 1-methylpentyl, 2-methylpentyl, 4-methyl-2-pentyl, 3,3-dimethyl-butyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the heteroaryl group includes one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzo-carbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, the arylene group has the same definition as the aryl group except for being divalent.

In the present specification, the heteroarylene group has the same definition as the heteroaryl group except for being divalent.

According to one embodiment of the present specification, Chemical Formula 1 is one of the following Chemical Formula 2 or 3.

Chemical Formula 2

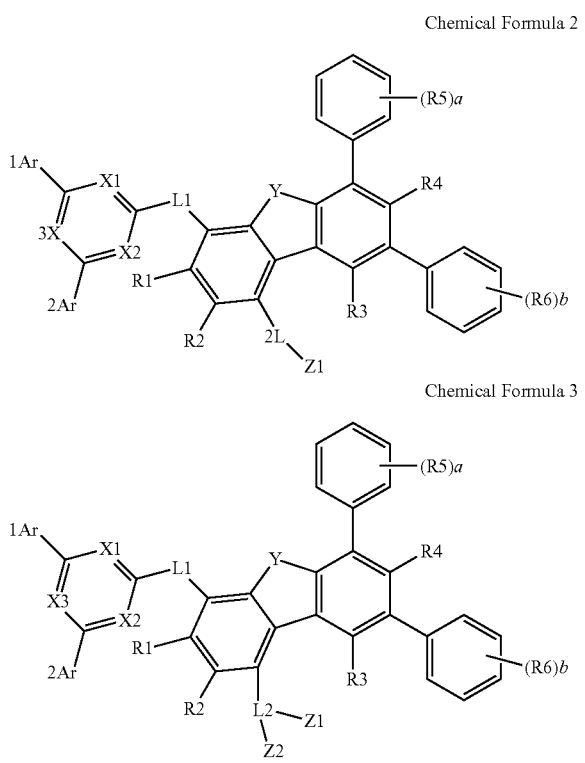

Chemical Formula 3

In Chemical Formulae 2 and 3, X1 to X3, L1, L2, Y, Ar1, Ar2, R1 to R6, n, a and b have the same definitions as in Chemical Formula 1, Z1 and Z2 are the same as or different from each other, and each independently is a nitrile group, a halogen group, a substituted or unsubstituted alkyl group, a substituted or unsubstituted silyl group, a substituted or unsubstituted aryl group, or a substituted or unsubstituted heteroaryl group.

According to one embodiment of the present specification, X1 and X2 are N, and X3 is CH.

According to one embodiment of the present specification, X1 and X3 are N, and X2 is CH.

According to one embodiment of the present specification, X2 and X3 are N, and X2 is CH.

According to one embodiment of the present specification, X1 to X3 are N.

According to one embodiment of the present specification, R1 to R6 are hydrogen.

According to one embodiment of the present specification, Y is O or S.

According to one embodiment of the present specification, Z1 and Z2 are the same as or different from each other, and each independently a nitrile group, a halogen group, a substituted or unsubstituted alkyl group having 1 to 10 carbon atoms, a silyl group that is unsubstituted or substituted with an alkyl group having 1 to 10 carbon atoms, a substituted or unsubstituted aryl group having 6 to 30 carbon atoms, or a substituted or unsubstituted heteroaryl group having 3 to 30 carbon atoms.

According to one embodiment of the present specification, Z1 and Z2 are the same as or different from each other, and each independently is a nitrile group, a halogen group, an alkyl group having 1 to 10 carbon atoms, a silyl group that is unsubstituted or substituted with an alkyl group having 1 to 10 carbon atoms, an aryl group having 6 to 30 carbon atoms, or a heteroaryl group having 3 to 30 carbon atoms, and the alkyl group having 1 to 10 carbon atoms, the silyl group that is unsubstituted or substituted with an alkyl group having 1 to 10 carbon atoms, the aryl group having 6 to 30 carbon atoms, or the heteroaryl group having 3 to 30 carbon atoms is unsubstituted or substituted with a halogen group, a nitrile group, a substituted or unsubstituted alkyl group, a substituted or unsubstituted silyl group, a substituted or unsubstituted aryl group, or a substituted or unsubstituted heteroaryl group.

According to one embodiment of the present specification, Z1 and Z2 are the same as or different from each other, and each independently is a nitrile group, a halogen group, an alkyl group having 1 to 10 carbon atoms, a silyl group that is unsubstituted or substituted with an alkyl group having 1 to 10 carbon atoms, an aryl group having 6 to 30 carbon atoms, or a heteroaryl group having 3 to 30 carbon atoms, and the alkyl group having 1 to 10 carbon atoms, the silyl group that is unsubstituted or substituted with an alkyl group having 1 to 10 carbon atoms, the aryl group having 6 to 30 carbon atoms, or the heteroaryl group having 3 to 30 carbon atoms is unsubstituted or substituted with a nitrile group, a fluoro group, a chloro group, a bromo group, an iodo group, a methyl group, an ethyl group, a propyl group, a butyl group, a tert-butyl group, a silyl group substituted with a methyl group, a phenyl group, a naphthyl group, a biphenyl group, a terphenyl group, a phenanthrene group, an anthracene group, a triphenylene group, a pyridine group, a pyrimidine group, a triazine group, a dibenzofuran group, a dibenzothiophene group, a carbazole group or a quinoline group.

According to one embodiment of the present specification, Z1 and Z2 are the same as or different from each other, and each independently is a phenyl group, a naphthyl group, a biphenyl group, a terphenyl group, a phenanthrene group, an anthracene group, a triphenylene group, a pyridine group, a pyrimidine group, a triazine group, a furan group, a thiophene group, a dibenzofuran group, a dibenzothiophene group, a carbazole group, a quinoline group, a benzothiazole group, or a benzoxazole group, and the phenyl group, the naphthyl group, the biphenyl group, the terphenyl group, the phenanthrene group, the anthracene group, the triphenylene group, the pyridine group, the pyrimidine group, the triazine group, the furan group, the thiophene group, the dibenzofuran group, the dibenzothiophene group, the carbazole group, the quinoline group, the benzothiazole group, or the benzoxazole group is unsubstituted or substituted with a nitrile group, a fluoro group, a chloro group, a bromo group, an iodo group, a methyl group, an ethyl group, a propyl group, a butyl group, a tert-butyl group, a silyl group substituted with a methyl group, a phenyl group, a naphthyl group, a biphenyl group, a terphenyl group, a phenanthrene group, an anthracene group, a triphenylene group, a pyridine group, a pyrimidine group, a triazine group, a dibenzofuran group, a dibenzothiophene group, a carbazole group or a quinoline group.

According to one embodiment of the present specification, Z1 and Z2 are the same as or different from each other, and each independently is a phenyl group that is unsubstituted or substituted with a nitrile group, a fluoro group, a tert-butyl group, a trimethylsilyl group or a phenyl group; a naphthyl group; a biphenyl group; a terphenyl group; a phenanthrene group; a triphenylene group; a pyridine group; a dibenzofuran group; a dibenzothiophene group; a carbazole group that is unsubstituted or substituted with a phenyl group; a quinoline group; a benzothiazole group; or a benzoxazole group.

According to one embodiment of the present specification, Z1 and Z2 are the same as or different from each other, and can each independently be any one substituent selected from among the following substituents:

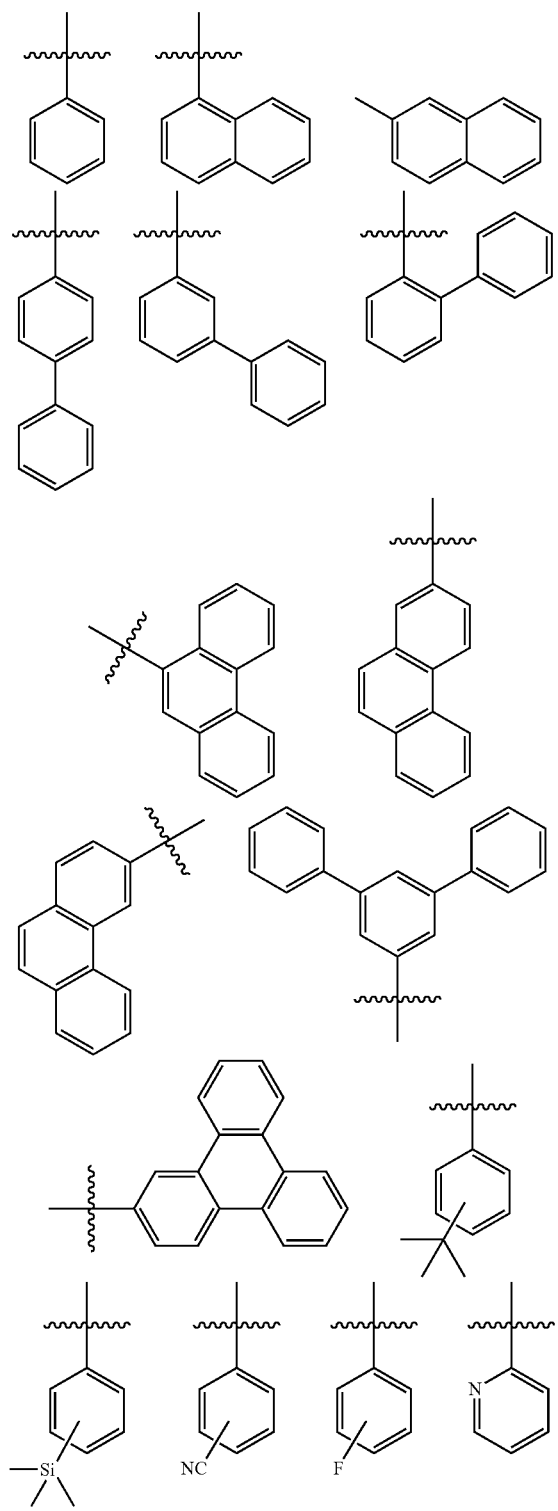

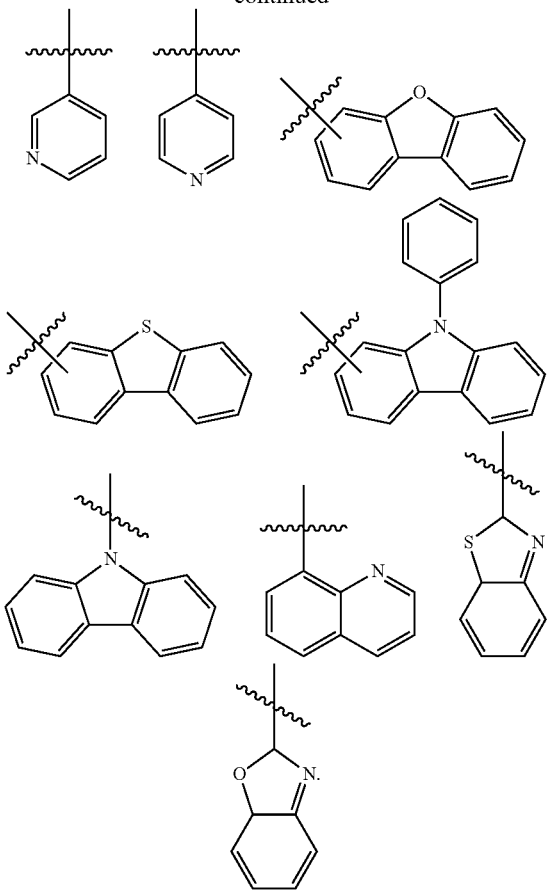

According to one embodiment of the present specification, Ar1 and Ar2 are the same as or different from each other, and each independently is a substituted or unsubstituted aryl group having 6 to 30 carbon atoms, or a substituted or unsubstituted heteroaryl group having 3 to 30 carbon atoms.

According to one embodiment of the present specification, Ar1 and Ar2 are the same as each other, and each is a substituted or unsubstituted aryl group having 6 to 30 carbon atoms, or a substituted or unsubstituted heteroaryl group having 3 to 30 carbon atoms.

According to one embodiment of the present specification, Ar1 and Ar2 are the same as each other, and each is a substituted or unsubstituted aryl group having 6 to 30 carbon atoms.

According to one embodiment of the present specification, Ar1 and Ar2 are the same as each other, and each is a substituted or unsubstituted heteroaryl group having 3 to 30 carbon atoms.

According to one embodiment of the present specification, Ar1 and Ar2 are different from each other, and each independently is a substituted or unsubstituted aryl group having 6 to 30 carbon atoms, or a substituted or unsubstituted heteroaryl group having 3 to 30 carbon atoms.

According to one embodiment of the present specification, Ar1 and Ar2 are different from each other, and each independently is a substituted or unsubstituted aryl group having 6 to 30 carbon atoms.

According to one embodiment of the present specification, Ar1 and Ar2 are different from each other, and each independently is a substituted or unsubstituted heteroaryl group having 3 to 30 carbon atoms.

According to one embodiment of the present specification, Ar1 and Ar2 are the same as or different from each other, and each independently is a substituted or unsubstituted monocyclic aryl group having 6 to 30 carbon atoms, a substituted or unsubstituted polycyclic aryl group having 10 to 30 carbon atoms, a substituted or unsubstituted monocyclic heteroaryl group having 3 to 30 carbon atoms, or a substituted or unsubstituted polycyclic heteroaryl group having 3 to 30 carbon atoms.

According to one embodiment of the present specification, Ar1 and Ar2 are the same as or different from each other, and each independently is a phenyl group, a biphenyl group, a naphthyl group, a terphenyl group, a fluorene group, a spirobifluorene group, a phenanthrene group, a triphenylene group, a carbazole group, a dibenzofuran group, a dibenzothiophene group, a benzonaphthofuran group, or a benzonaphthothiophene group, and the phenyl group, the biphenyl group, the naphthyl group, the terphenyl group, the fluorene group, the spirobifluorene group, the phenanthrene group, the triphenylene group, the carbazole group, the dibenzofuran group, the dibenzothiophene group, the benzonaphthofuran group, or the benzonaphthothiophene group is unsubstituted or substituted with one or more substituents selected from the group consisting of deuterium; a halogen group; an alkyl group having 1 to 10 carbon atoms; an aryl group having 6 to 20 carbon atoms unsubstituted or substituted with an alkyl group having 1 to 10 carbon atoms or an aryl group having 6 to 30 carbon atoms; and a heteroaryl group having 3 to 30 carbon atoms unsubstituted or substituted with an aryl group having 6 to 30 carbon atoms.

According to one embodiment of the present specification, Ar1 and Ar2 are the same as or different from each other, and each independently is a phenyl group, a biphenyl group, a naphthyl group, a terphenyl group, a fluorene group, a spirobifluorene group, a phenanthrene group, a triphenylene group, a carbazole group, a dibenzofuran group, a dibenzothiophene group, a benzonaphthofuran group, or a benzonaphthothiophene group, and the phenyl group, the biphenyl group, the naphthyl group, the terphenyl group, the fluorene group, the spirobifluorene group, the phenanthrene group, the triphenylene group, the carbazole group, the dibenzofuran group, the dibenzothiophene group, the benzonaphthofuran group, or the benzonaphthothiophene group is unsubstituted or substituted with one or more substituents selected from the group consisting of deuterium, a phenyl group, a naphthyl group, and a methyl group.

According to one embodiment of the present specification, Ar1 and Ar2 are the same as or different from each other, and each independently is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

According to one embodiment of the present specification, Ar1 and Ar2 are the same as each other, and each is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

According to one embodiment of the present specification, Ar1 and Ar2 are different from each other, and each independently is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

According to one embodiment of the present specification, Ar1 is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

According to one embodiment of the present specification, Ar2 is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

According to one embodiment of the present specification, L1 and L2 are the same as or different from each other, and each independently is a direct bond, or a substituted or unsubstituted arylene group.

According to one embodiment of the present specification, L1 and L2 are the same as or different from each other, and each independently is a direct bond, or a substituted or unsubstituted arylene group having 6 to 30 carbon atoms.

According to one embodiment of the present specification, L1 and L2 are the same as or different from each other, and each independently is a direct bond, or a monocyclic substituted or unsubstituted arylene group having 6 to 30 carbon atoms.

According to one embodiment of the present specification, L1 and L2 are the same as or different from each other, and each independently is a direct bond, or a polycyclic substituted or unsubstituted arylene group having 10 to 30 carbon atoms.

According to one embodiment of the present specification, L1 and L2 are the same as or different from each other, and each independently is a substituted or unsubstituted phenylene group, a substituted or unsubstituted naphthylene group, a substituted or unsubstituted divalent biphenyl group, a substituted or unsubstituted divalent terphenyl group, a substituted or unsubstituted divalent quaterphenyl group, a substituted or unsubstituted divalent fluorene group, a substituted or unsubstituted divalent anthracene group, a substituted or unsubstituted divalent pyrene group, a substituted or unsubstituted divalent triphenylene group, or a substituted or unsubstituted divalent phenanthrene group.

According to one embodiment of the present specification, L1 and L2 are the same as or different from each other, and each independently is a phenylene group that is unsubstituted or substituted with an alkyl group having 1 to 10 carbon atoms, a naphthylene group that is unsubstituted or substituted with an alkyl group having 1 to 10 carbon atoms, a divalent biphenyl group that is unsubstituted or substituted with an alkyl group having 1 to 10 carbon atoms, a divalent terphenyl group that is unsubstituted or substituted with an alkyl group having 1 to 10 carbon atoms, a divalent quaterphenyl group that is unsubstituted or substituted with an alkyl group having 1 to 10 carbon atoms, a divalent fluorene group that is unsubstituted or substituted with an alkyl group having 1 to 10 carbon atoms, a divalent anthracene group that is unsubstituted or substituted with an alkyl group having 1 to 10 carbon atoms, a divalent pyrene group that is unsubstituted or substituted with an alkyl group having 1 to 10 carbon atoms, a divalent triphenylene group that is unsubstituted or substituted with an alkyl group having 1 to 10 carbon atoms, or a divalent phenanthrene group that is unsubstituted or substituted with an alkyl group having 1 to 10 carbon atoms.

According to one embodiment of the present specification, L1 and L2 are the same as or different from each other, and each independently is a phenylene group, a naphthylene group, a divalent biphenyl group, a divalent terphenyl group, a divalent quaterphenyl group, a divalent fluorene group that is unsubstituted or substituted with an alkyl group having 1 to 10 carbon atoms, a divalent anthracene group, a divalent pyrene group, a divalent triphenylene group, or a divalent phenanthrene group.

According to one embodiment of the present specification, L1 is a direct bond.

According to one embodiment of the present specification, L1 is a phenylene group.

According to one embodiment of the present specification, L1 is a divalent naphthyl group.

According to one embodiment of the present specification, L2 is a direct bond.

According to one embodiment of the present specification, L2 is a phenylene group.

According to one embodiment of the present specification, L2 is a divalent naphthyl group. According to one embodiment of the present specification, in Chemical Formula 1, Z is a substituted or unsubstituted aryl group having 6 to 30 carbon atoms, or a substituted or unsubstituted heteroaryl group having 3 to 30 carbon atoms and including any one or more of N, O and S.

According to another embodiment of the present specification, the heterocyclic compound of Chemical Formula 1 can be any one of the following compounds:

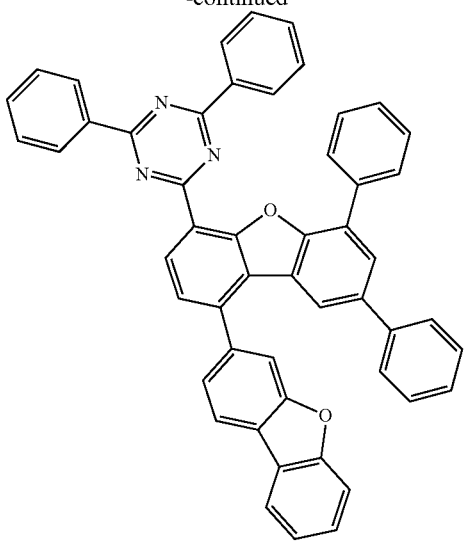

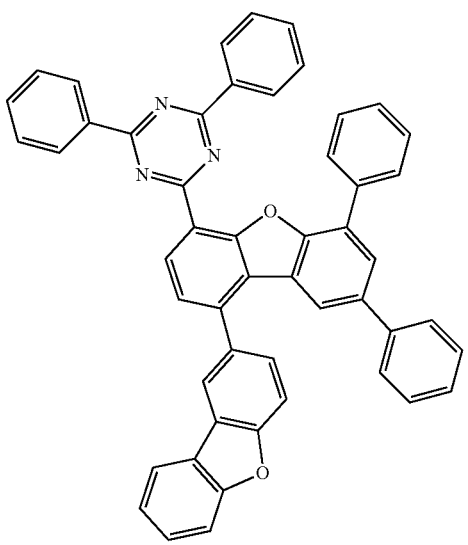

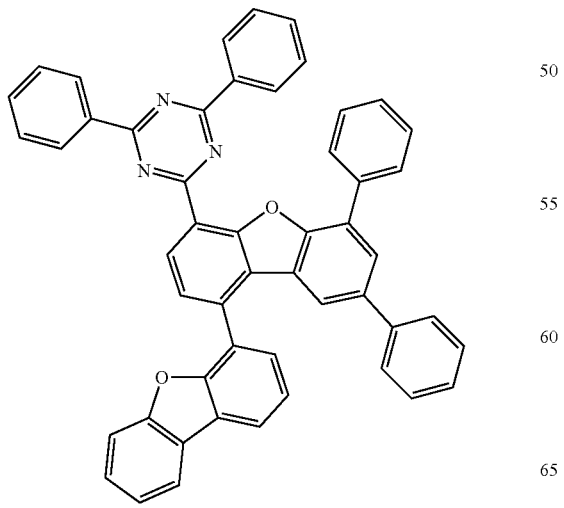

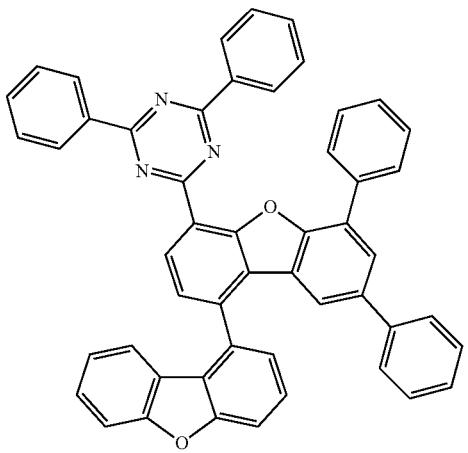

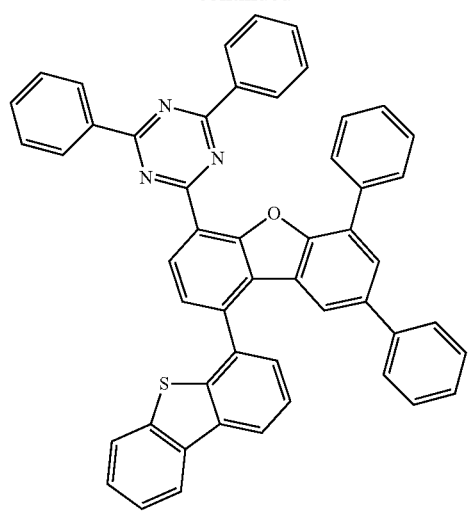
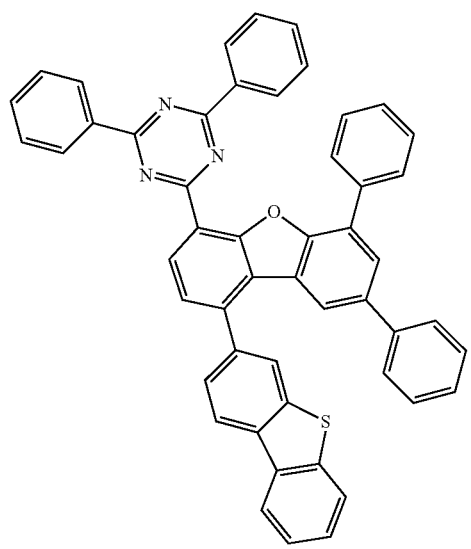
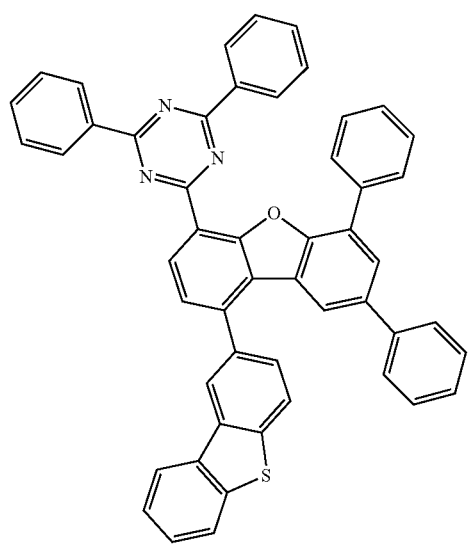
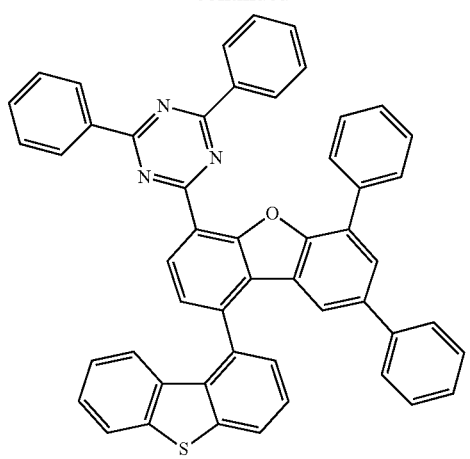
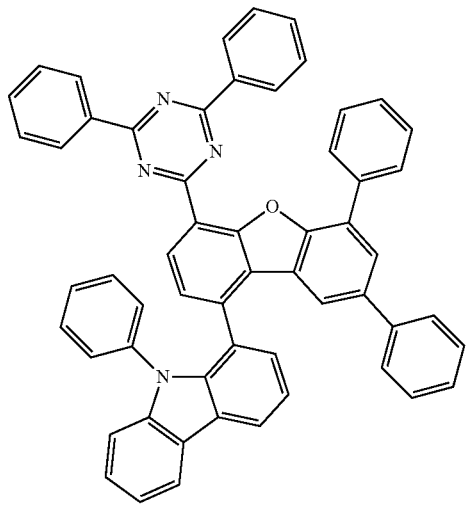
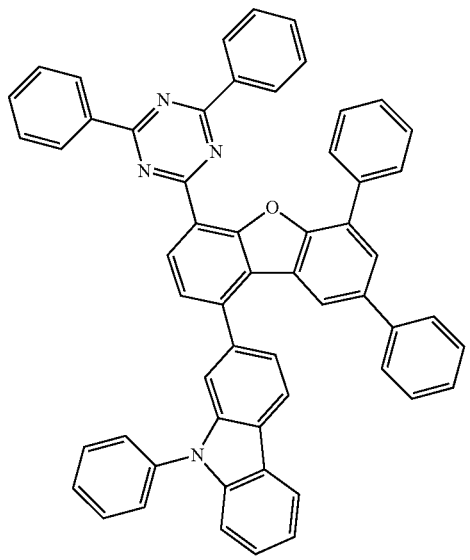

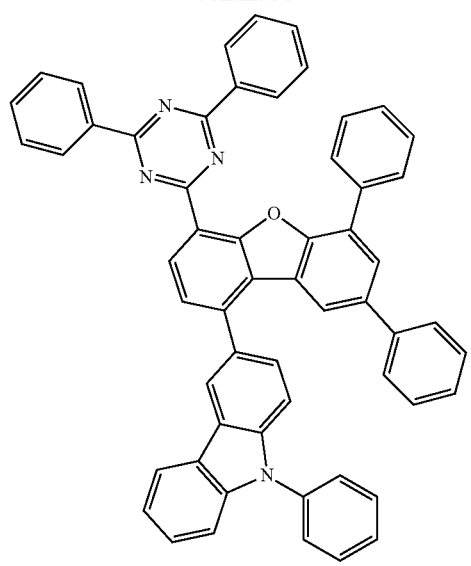
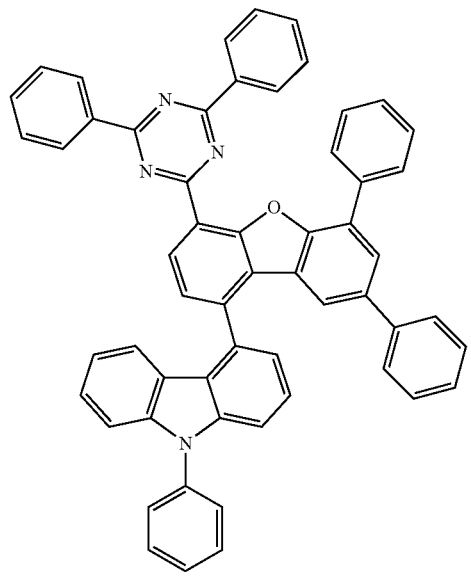
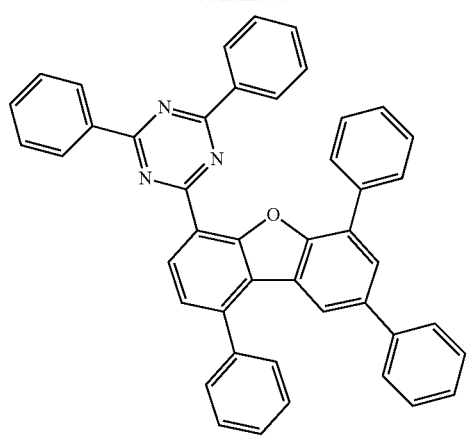
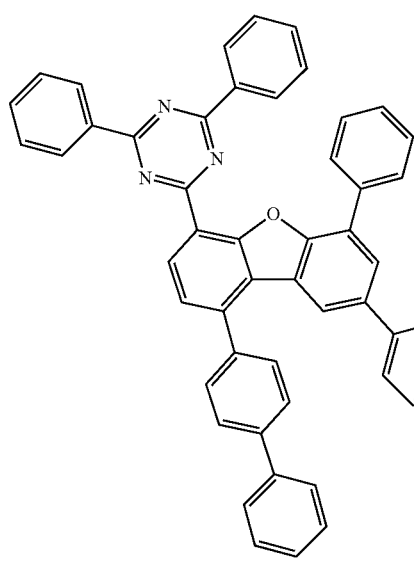
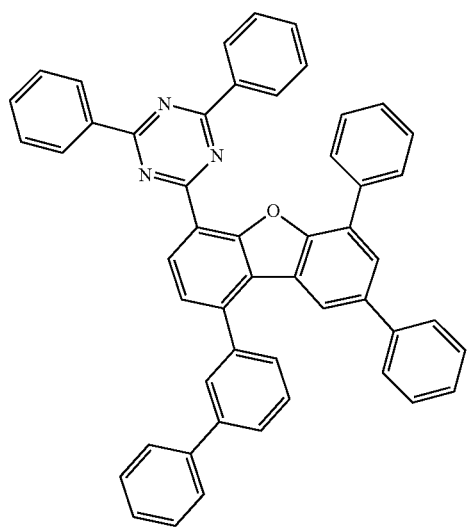

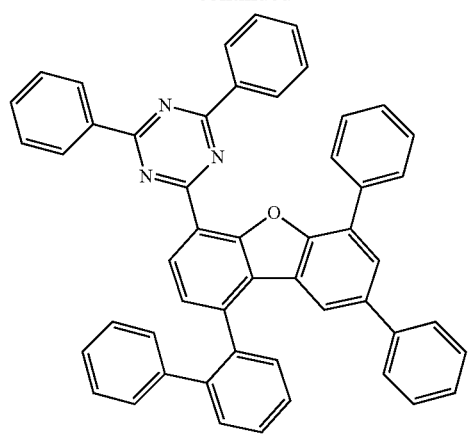
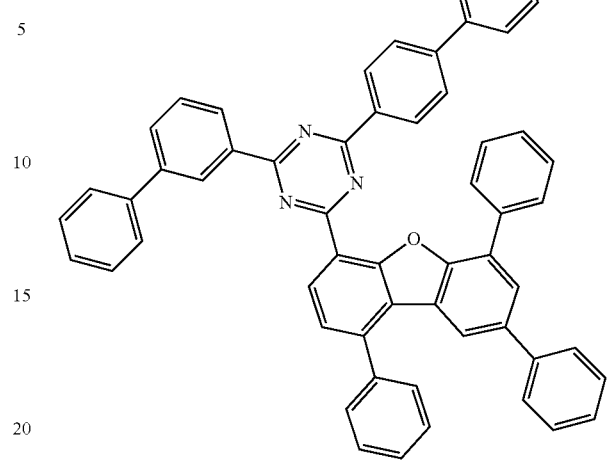
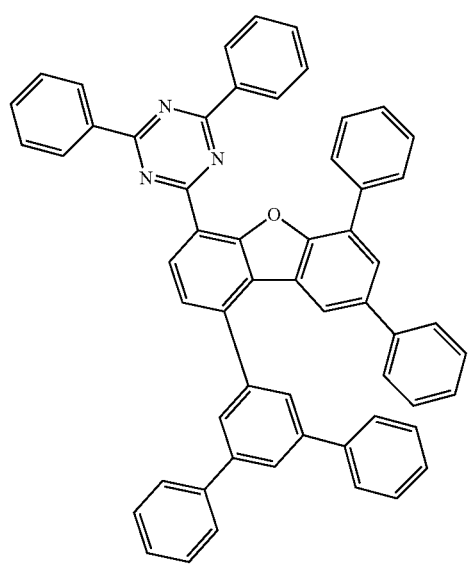
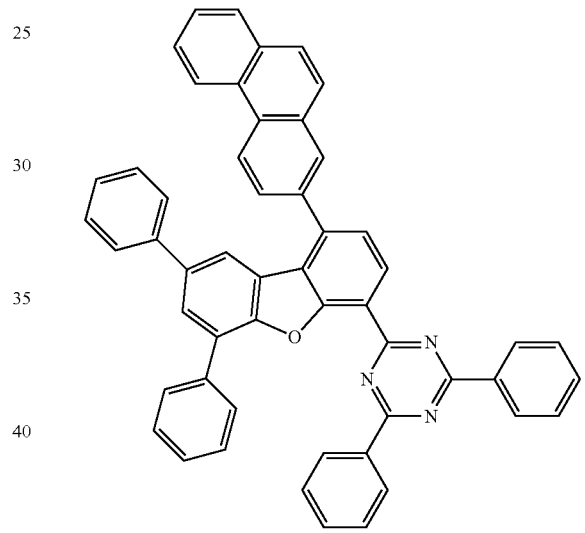
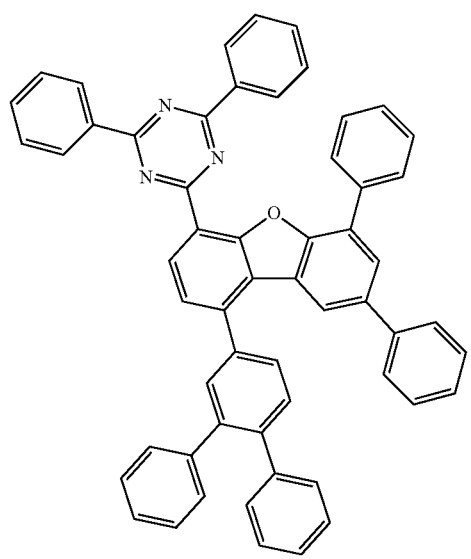
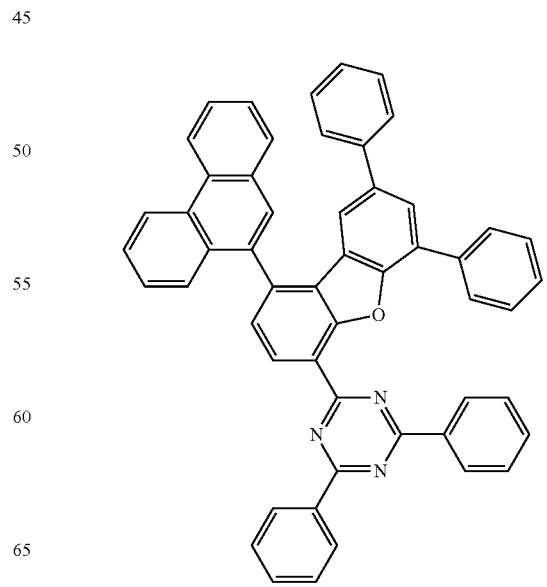

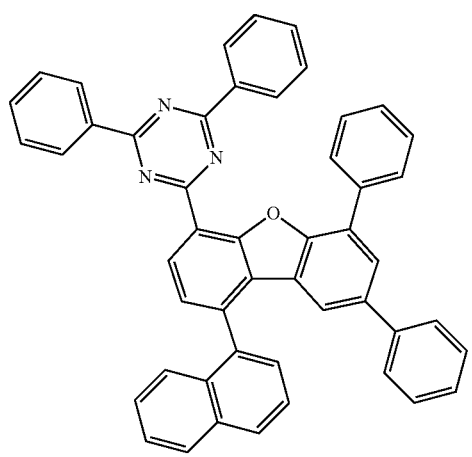
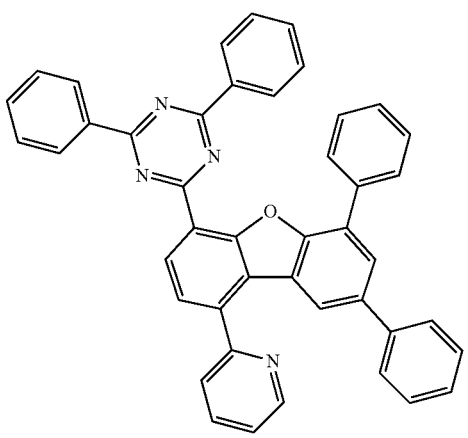
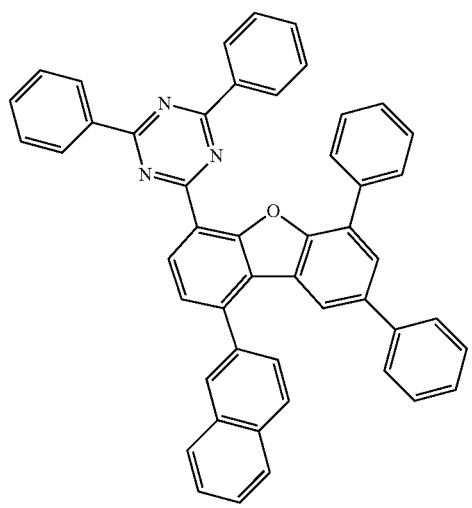
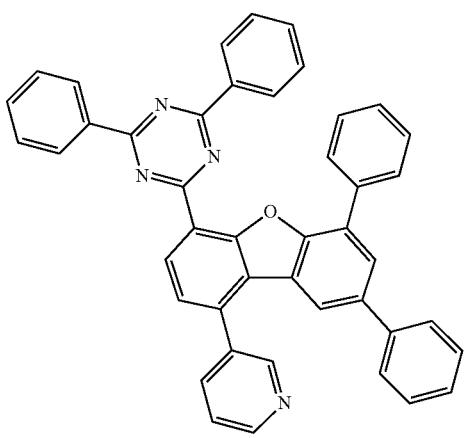
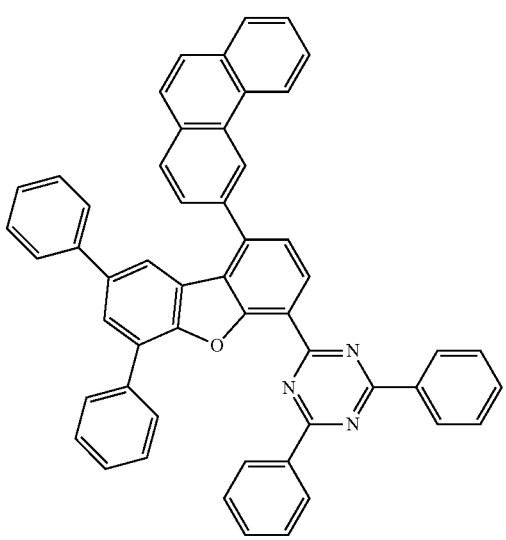
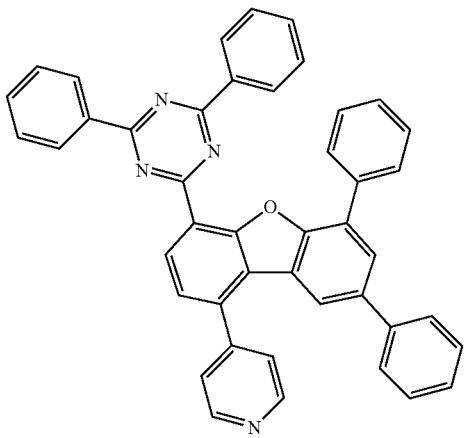

-continued
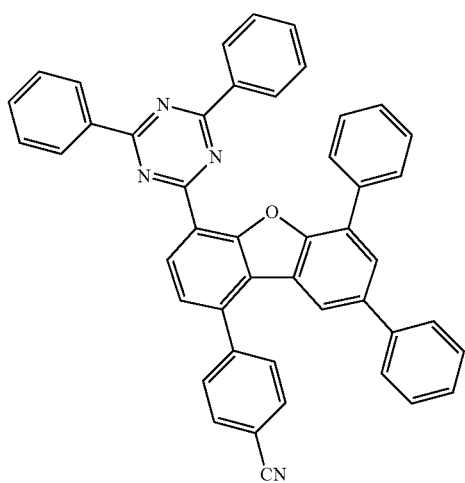
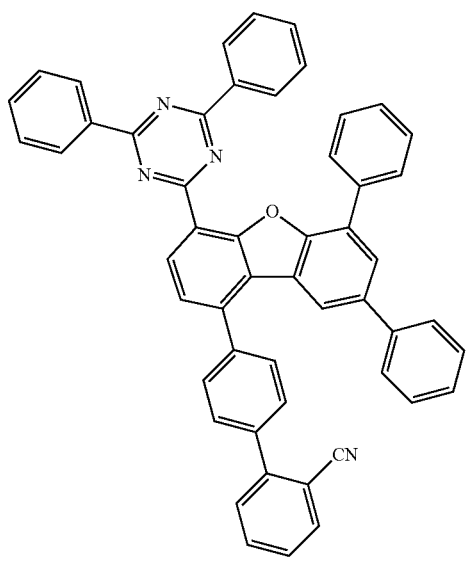
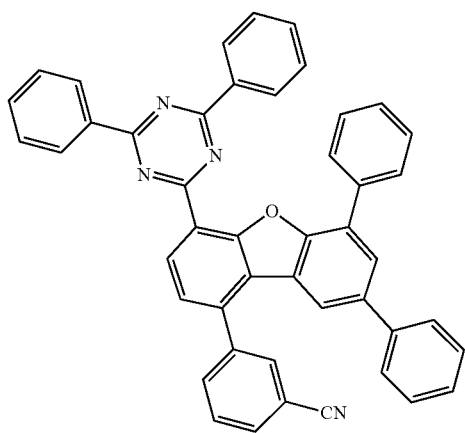
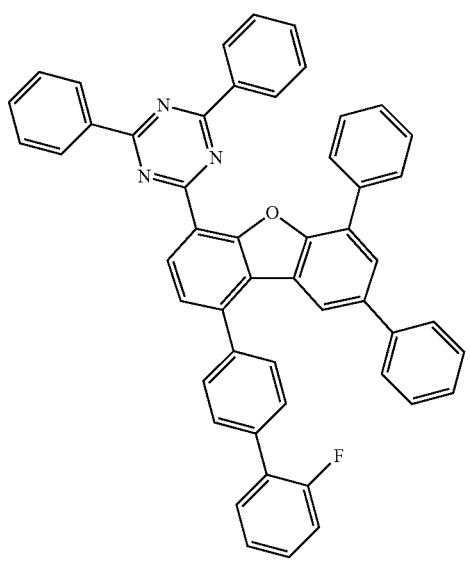
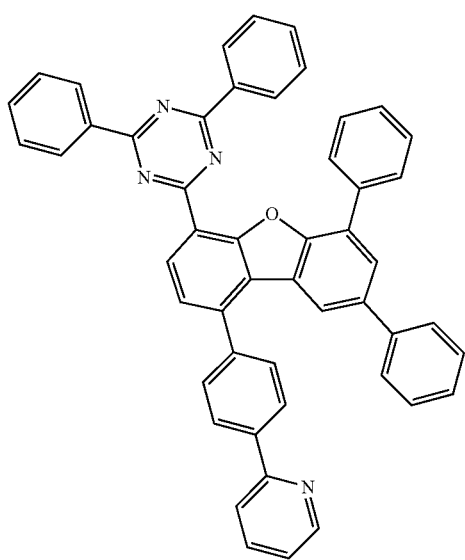

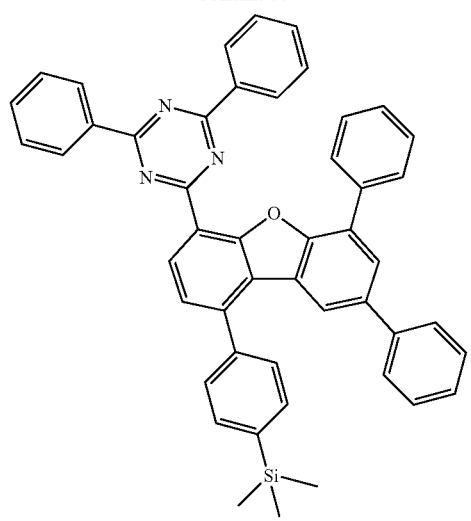
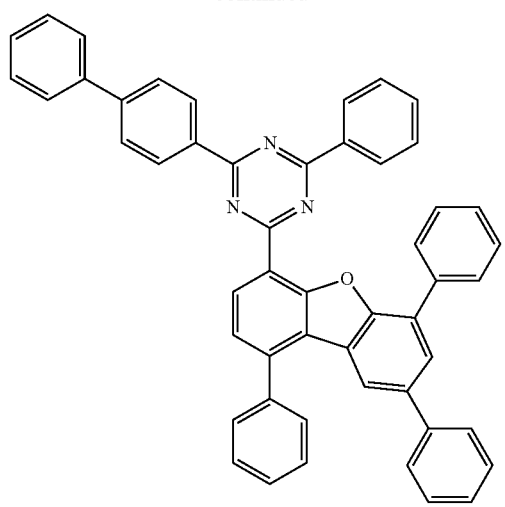
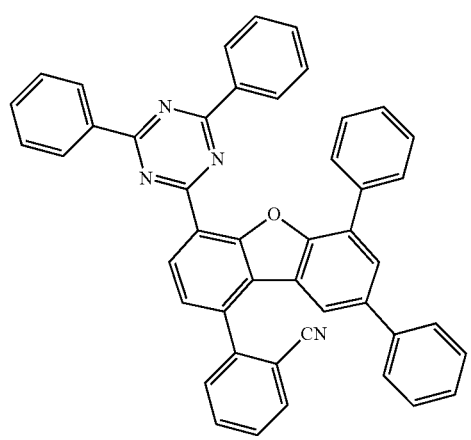
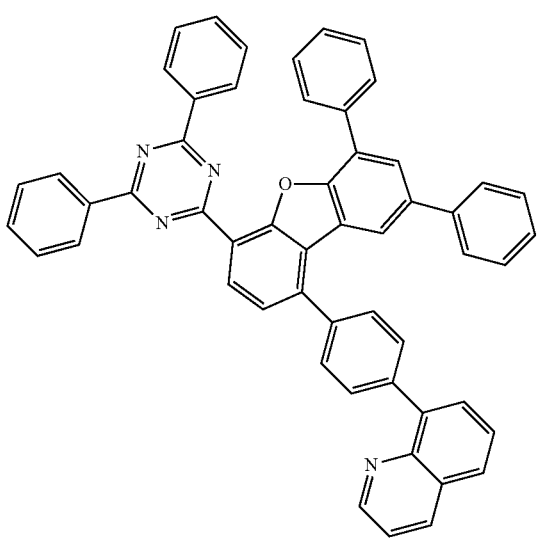
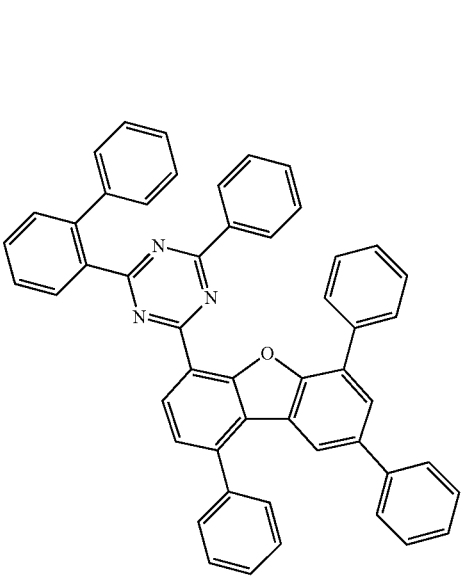

25
-continued
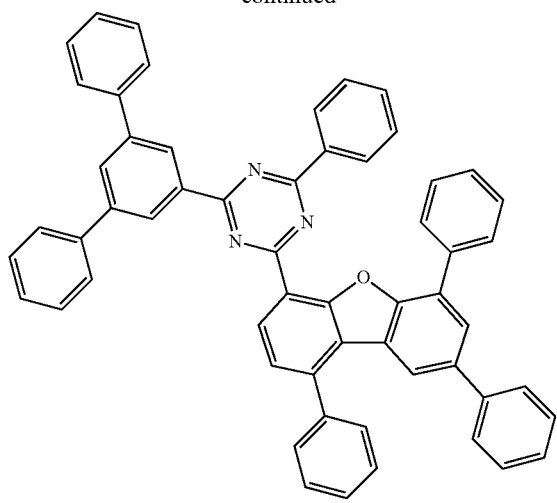
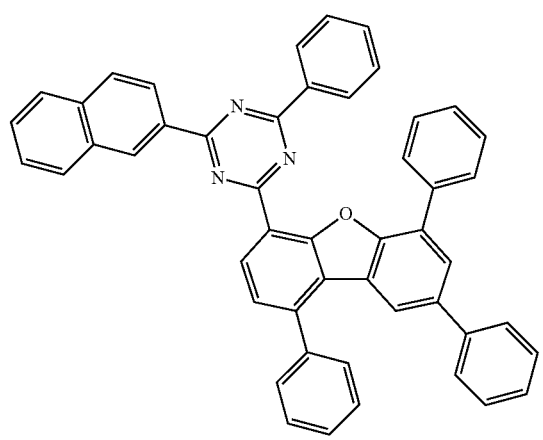
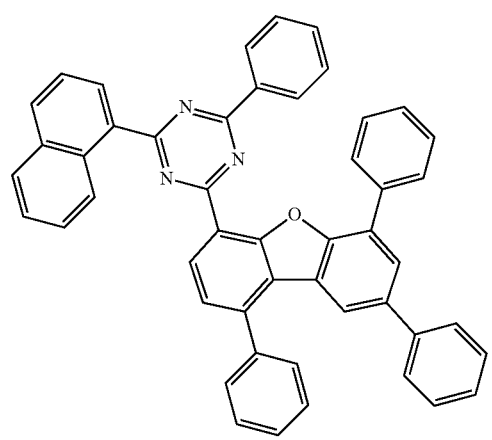
26
-continued
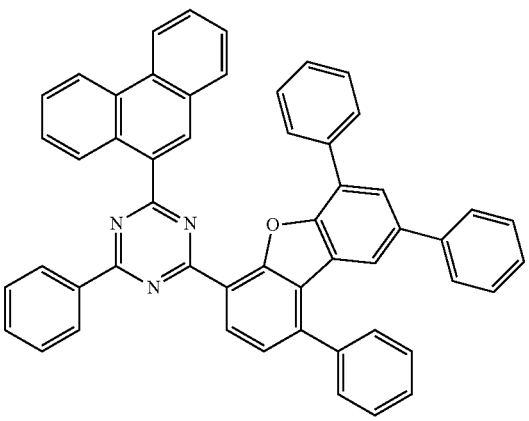
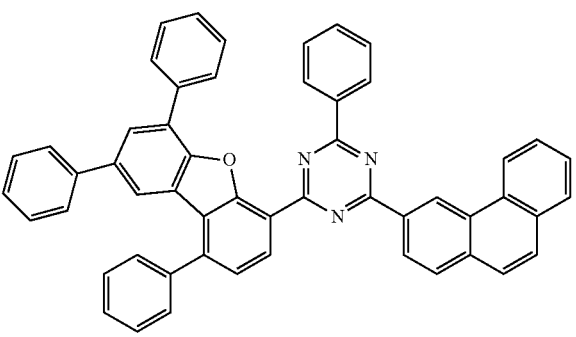
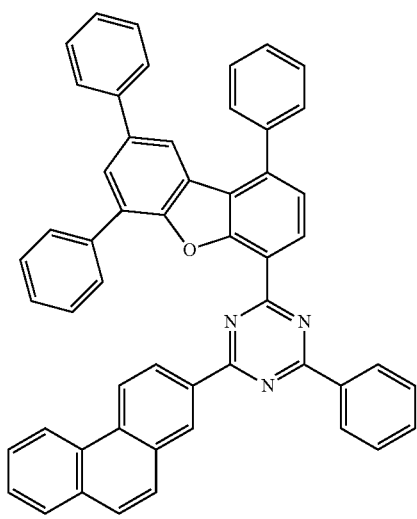

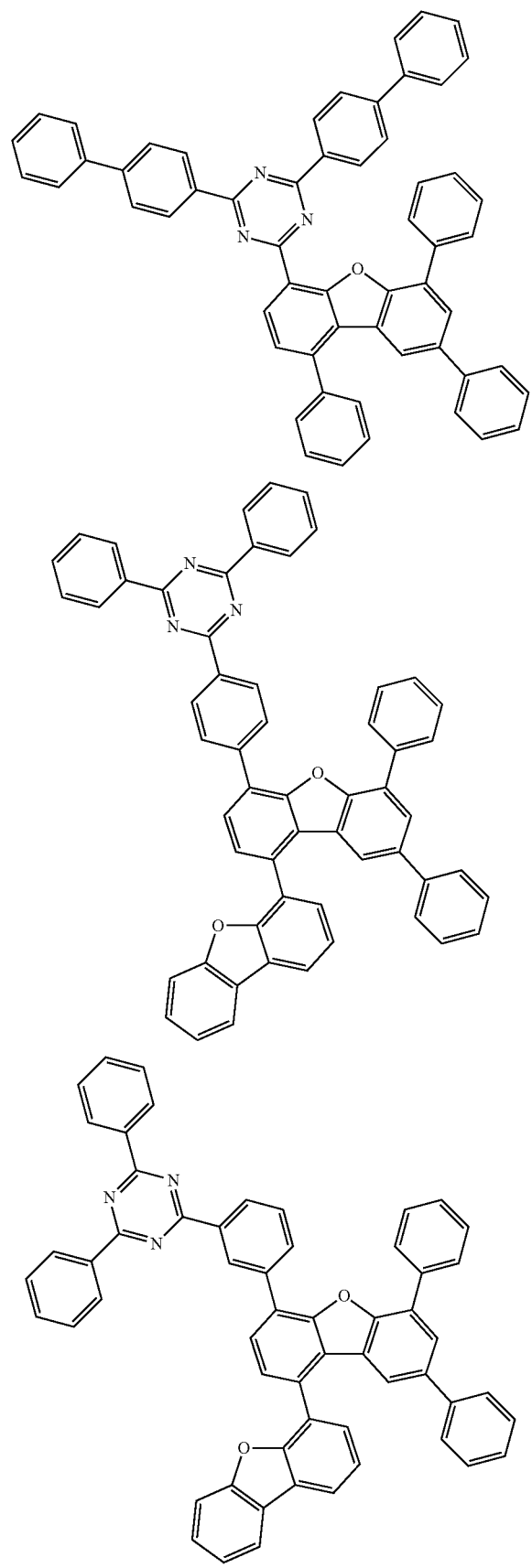
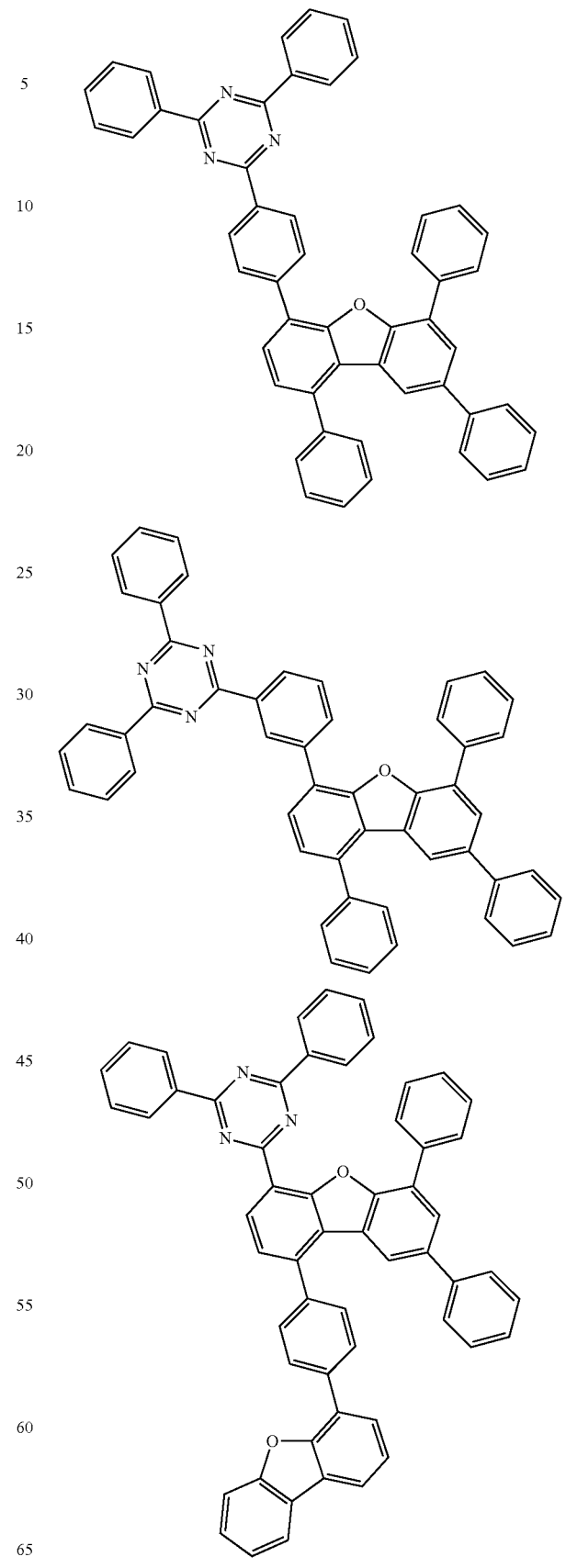

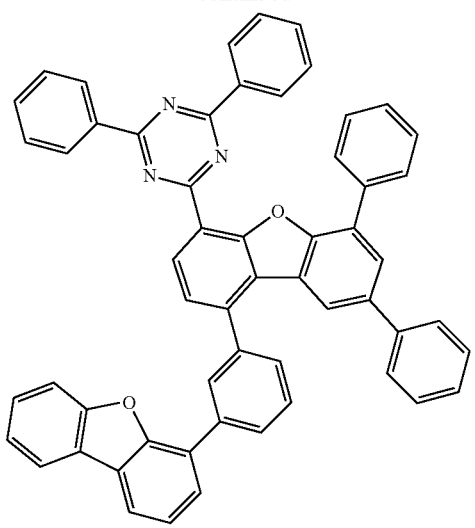
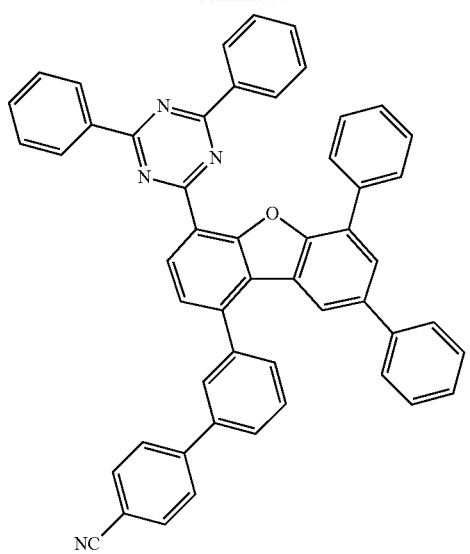
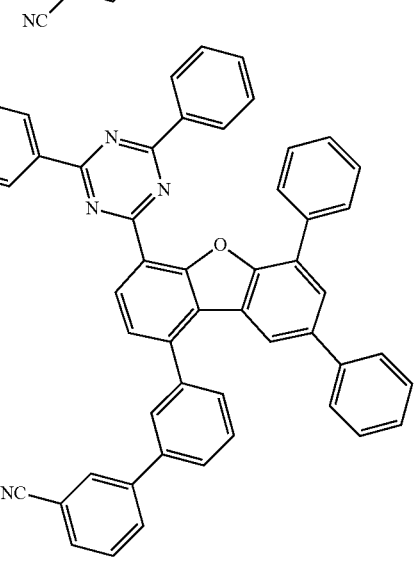
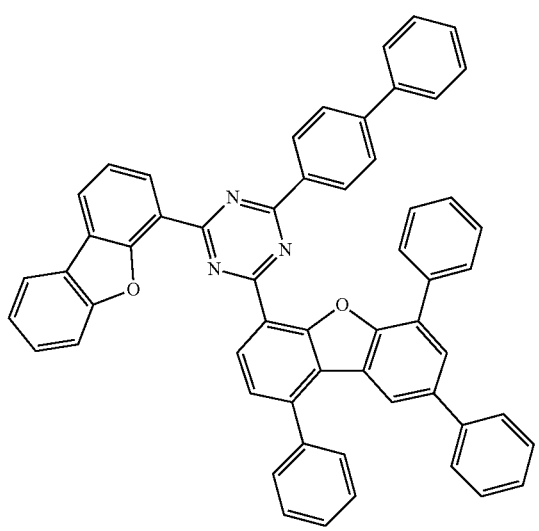
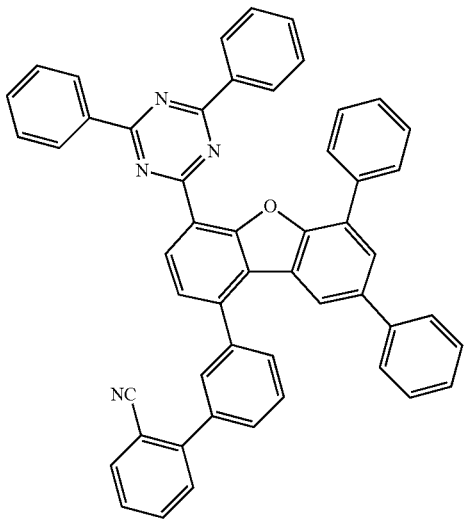

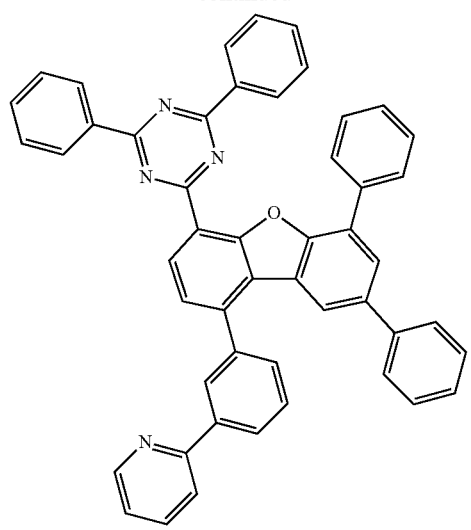
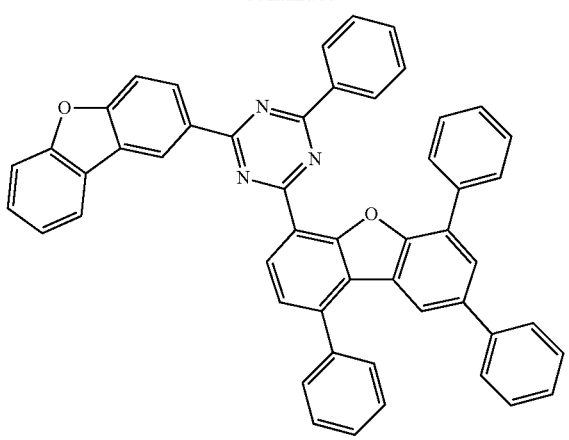
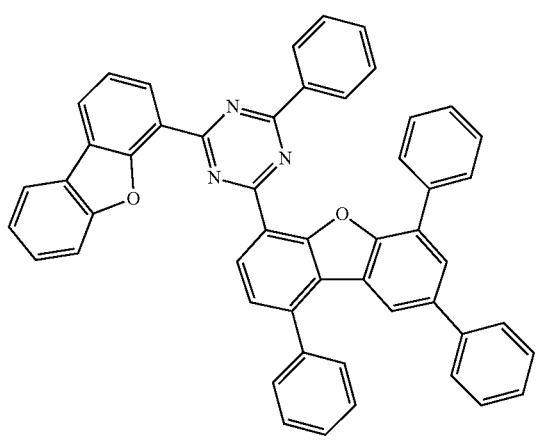
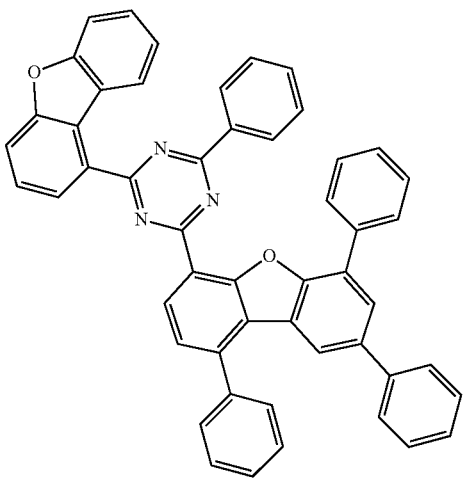
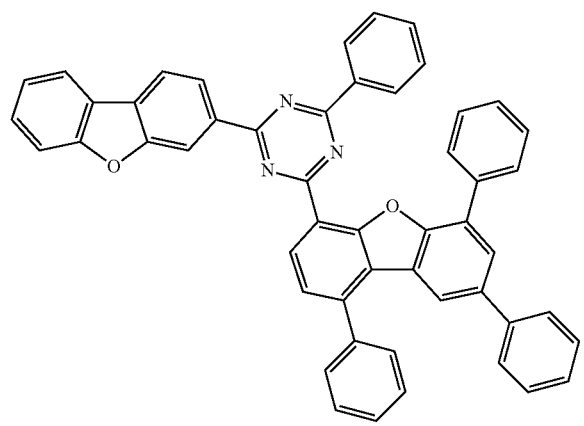
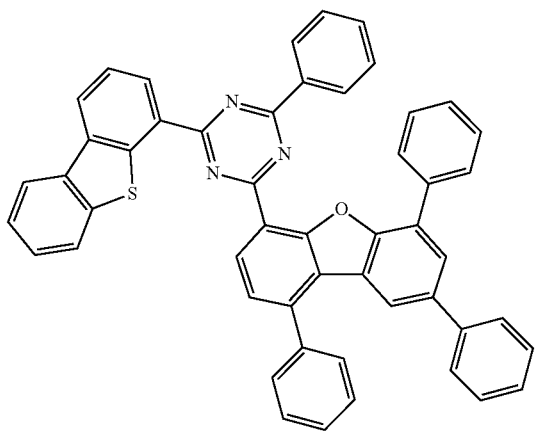

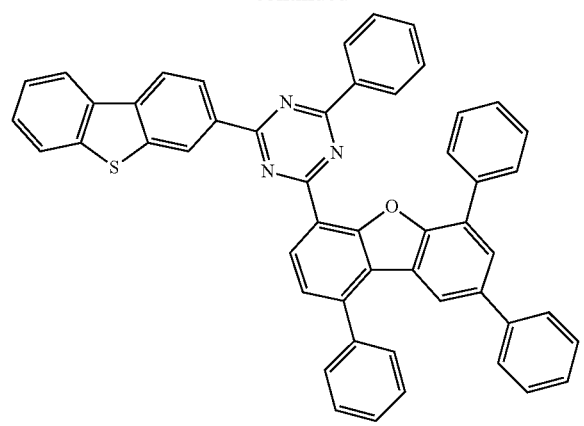
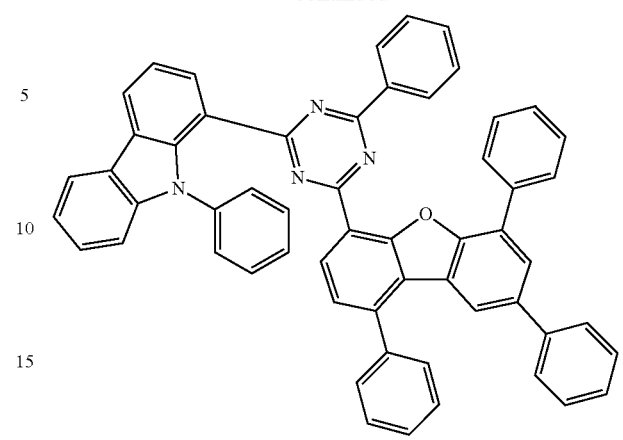
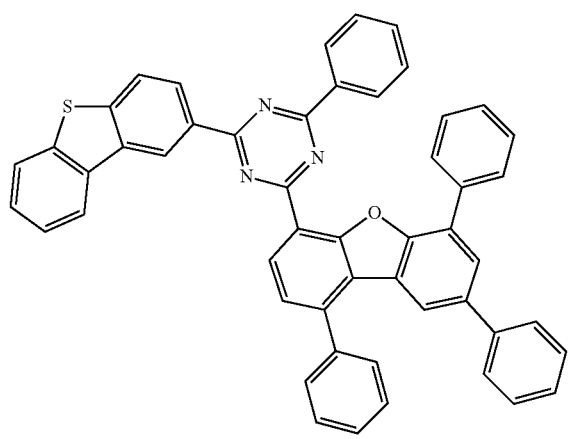
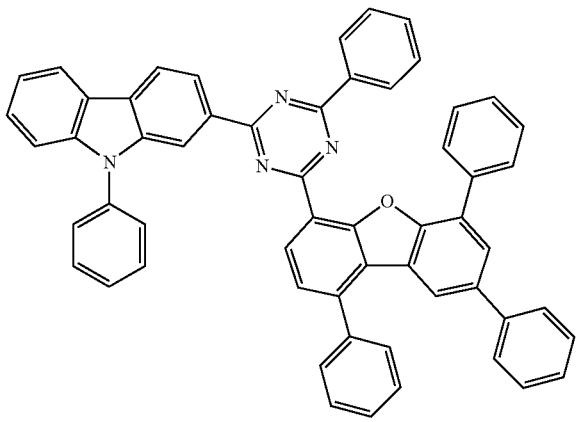
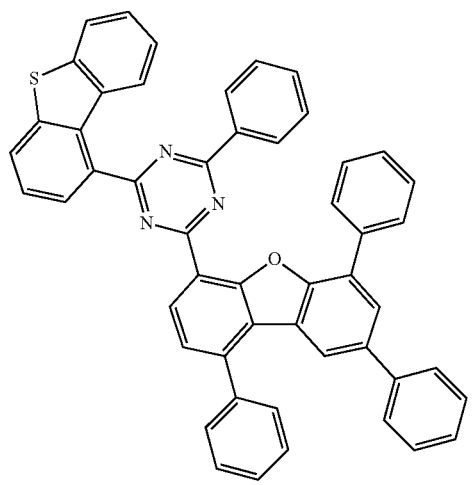
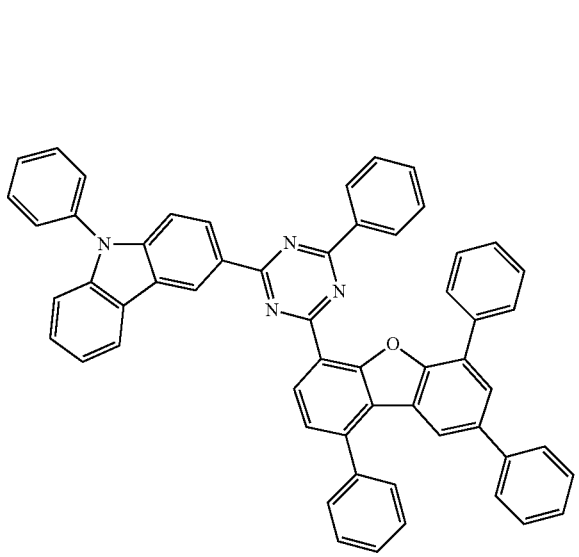

-continued

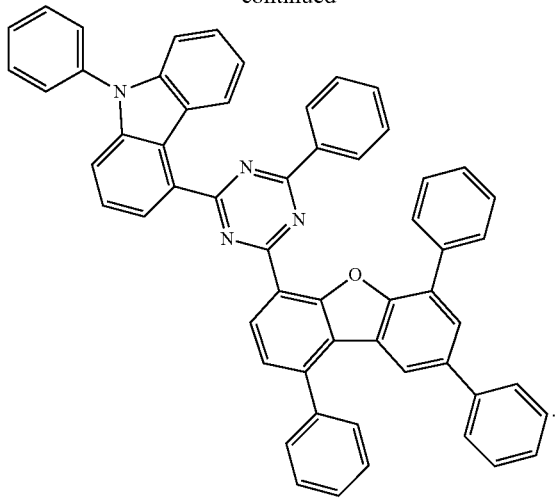 [SMILES: c1ccc(-c2cc(-c3ccccc3)c3oc4c(-c5nc(-c6ccccc6)nc(-c6cccc7c6c6ccccc6n7-c6ccccc6)n5)ccc(-c5ccccc5)c4c3c2)cc1]

The organic material layer of the organic light emitting device of the present disclosure can be formed in a single layer structure, but can be formed in a multilayer structure in which two or more organic material layers are laminated. For example, the organic light emitting device of the present disclosure includes a first electrode; a second electrode provided opposite to the first electrode; and one, two or more organic material layers provided between the first electrode and the second electrode, wherein one or more layers of the organic material layers can include the heterocyclic compound described above.

FIG. 1 illustrates a structure of the organic light emitting device in which a first electrode (2), an organic material layer (3) and a second electrode (4) are consecutively laminated on a substrate (1).

FIG. 2 illustrates a structure of the organic light emitting device in which a first electrode (2), a hole injection layer (5), a hole transfer layer (6), an electron blocking layer (7), a light emitting layer (8), an electron transfer layer (9), an electron injection layer (10) and a second electrode (4) are consecutively laminated on a substrate (1). The heterocyclic compound of Chemical Formula 1 can be preferably included in the light emitting layer.

However, the structure of the organic light emitting device according to one embodiment of the present specification is not limited to FIGS. 1 and 2, and can be any one of the following structures:

(1) an anode/a hole transfer layer/a light emitting layer/an electron transfer layer/a cathode;
(2) an anode/a hole transfer layer/a light emitting layer/an electron transfer layer/an electron injection layer/a cathode;
(3) an anode/a hole injection layer/a hole transfer layer/a light emitting layer/an electron transfer layer/an electron injection layer/a cathode;
(4) an anode/a hole transfer layer/a hole control layer/a light emitting layer/an electron transfer layer/an electron injection layer/a cathode;
(5) an anode/a hole injection layer/a hole transfer layer/a hole control layer/a light emitting layer/an electron transfer layer/an electron injection layer/a cathode;
(6) an anode/a hole transfer layer/a light emitting layer/an electron control layer/an electron transfer layer/a cathode;
(7) an anode/a hole transfer layer/a light emitting layer/an electron control layer/an electron transfer layer/an electron injection layer/a cathode;
(8) an anode/a hole injection layer/a hole transfer layer/a light emitting layer/an electron control layer/an electron transfer layer/a cathode; or
(9) an anode/a hole injection layer/a hole transfer layer/a light emitting layer/an electron control layer/an electron transfer layer/an electron injection layer/a cathode.

The organic light emitting device of the present disclosure includes a structure in which a first electrode, an organic material layer and a second electrode are consecutively laminated on a substrate, and the organic material layer can include the compound of Chemical Formula 1.

In one embodiment of the present disclosure, the organic material layer includes a light emitting layer, and the light emitting layer can include the compound of Chemical Formula 1.

In one embodiment of the present disclosure, the organic material layer includes a light emitting layer, and the light emitting layer can include the compound of Chemical Formula 1 as a host.

In one embodiment of the present disclosure, the organic material layer includes a light emitting layer, and the light emitting layer can include an additional host material in addition to the compound of Chemical Formula 1.

According to one embodiment of the present specification, the light emitting layer including the compound of the present disclosure can include an organic compound as the additional host material.

According to one embodiment of the present specification, the light emitting layer including the compound of the present disclosure can include an N-containing heterocyclic compound as the additional host material.

According to one embodiment of the present specification, the light emitting layer including the compound of the present disclosure can include a biscarbazole compound as the additional host material.

According to one embodiment of the present specification, the light emitting layer including the compound of the present disclosure can include an additional host material, and as one example, the light emitting layer can include a compound of the following Chemical Formula B:

Chemical Formula B

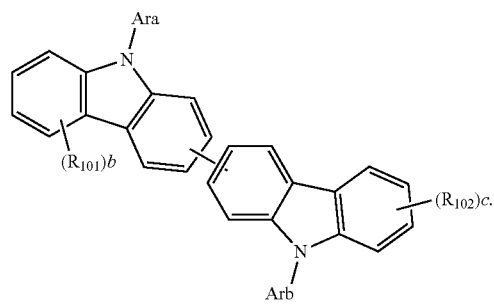

In Chemical Formula B:

Ara and Arb are the same as or different from each other, and each independently is an aryl group that is unsubstituted or substituted with a heteroaryl group; or a heteroaryl group that is unsubstituted or substituted with an aryl group;

$R_{101}$ and $R_{102}$ are the same as or different from each other, and each independently is hydrogen; deuterium; an aryl group that is unsubstituted or substituted with a heteroaryl group; or a heteroaryl group that is unsubstituted or substituted with an aryl group, or adjacent groups bond to each other to form a substituted or unsubstituted aromatic hydrocarbon ring, and b and c are each an integer of 0 to 4.

In one embodiment of the present disclosure, the organic material layer includes a light emitting layer, and the light emitting layer can include a host and a dopant in a mass ratio of 99:1 to 50:50.

In one embodiment of the present disclosure, the organic material layer includes a light emitting layer, and the light emitting layer can include a host and a dopant in a mass ratio of 99:1 to 80:20.

In one embodiment of the present disclosure, the organic material layer includes a light emitting layer, and the light emitting layer can include a sum of a first host and a second host: a dopant in a mass ratio of 98:2 to 80:20.

In one embodiment of the present disclosure, the first host and the second host can be included in a ratio of 1:9 to 9:1.

In one embodiment of the present disclosure, the first host and the second host can be included in a ratio of 3:7 to 7:3.

In one embodiment of the present disclosure, the organic material layer includes a light emitting layer, the light emitting layer can include a metal complex as a dopant, and an iridium complex or a platinum complex can be used as the metal complex, however, the metal complex is not limited thereto.

In one embodiment of the present disclosure, the organic material layer includes a light emitting layer, and the light emitting layer can include an iridium complex as a dopant.

In one embodiment of the present disclosure, the organic material layer includes an electron injection layer, an electron transfer layer, or an electron injection and transfer layer, and the electron injection layer, the electron transfer layer, or the electron injection and transfer layer can include the compound of Chemical Formula 1.

In one embodiment of the present disclosure, the organic material layer includes an electron injection layer, an electron transfer layer, or an electron injection and transfer layer, and the electron injection layer, the electron transfer layer, or the electron injection and transfer layer can include an organic compound and a metal in a mass ratio of 99:1 to 1:99.

In one embodiment of the present disclosure, the organic material layer includes an electron injection layer, an electron transfer layer, or an electron injection and transfer layer, and the electron injection layer, the electron transfer layer, or the electron injection and transfer layer can include an organic compound and a metal in a mass ratio of 99:1 to 1:1.

In one embodiment of the present disclosure, the electron injection layer, the electron transfer layer, or the electron injection and transfer layer can include a naphthalene derivative as the organic compound, however, the organic compound is not limited thereto.

In one embodiment of the present disclosure, the electron injection layer, the electron transfer layer, or the electron injection and transfer layer can include lithium as the metal, however, the metal is not limited thereto.

In one embodiment of the present disclosure, the organic material layer includes a hole injection layer, a hole transfer layer, or a hole injection and transfer layer, and the hole injection layer, the hole transfer layer, or the hole injection and transfer layer can include the compound of Chemical Formula 1.

In one embodiment of the present disclosure, the organic material layer includes a hole blocking layer, and the hole blocking layer can include the compound of Chemical Formula 1.

In one embodiment of the present disclosure, the organic material layer includes an electron blocking layer, and the electron blocking layer can include the compound of Chemical Formula 1.

According to one embodiment of the present disclosure, the first electrode is an anode, and the second electrode is a cathode.

According to one embodiment of the present disclosure, the second electrode is an anode, and the first electrode is a cathode.

In one embodiment of the present disclosure, the organic material layer including the compound of Chemical Formula 1 includes at least one of an electron injection layer, an electron transfer layer, a layer carrying out electron injection and electron transfer at the same time, and at least one of the layers can include the compound of Chemical Formula 1.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylcompound), poly[3,4-(ethylene-1,2-dioxy)compound] (PEDT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, polyaniline, and polycompound-based conductive polymers, and the like, but are not limited thereto.

The hole transfer material is a material capable of receiving holes from an anode or a hole injection layer, moving the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto.

The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, heterocyclic compounds, dibenzofuran derivatives, ladder-type furan compounds, pyrimidine derivatives and the like can be included, however, the host material is not limited thereto.

When the organic light emitting device includes a plurality of organic material layers, the organic material layers can be formed with materials the same as or different from each other.

The organic light emitting device of the present specification can be manufactured using materials and methods known in the art, except that one of more layers of the organic material layers are formed using the heterocyclic compound.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

The hole blocking layer is a layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The organic light emitting device according to the present specification can be a top-emission type, a bottom-emission type or a dual-emission type depending on the materials used.

EXAMPLES

A method for preparing the heterocyclic compound of Chemical Formula 1 and a method for manufacturing an organic light emitting device using the same will be specifically described in the following examples. However, the following examples are for illustrative purposes only, and the scope of the present disclosure is not limited thereby.

By varying substituent types and substituting positions in the following preparation methods, all the compounds described in the present specification can be prepared.

Synthesis Example

<Synthesis Example 1>—Preparation of Intermediate A-5

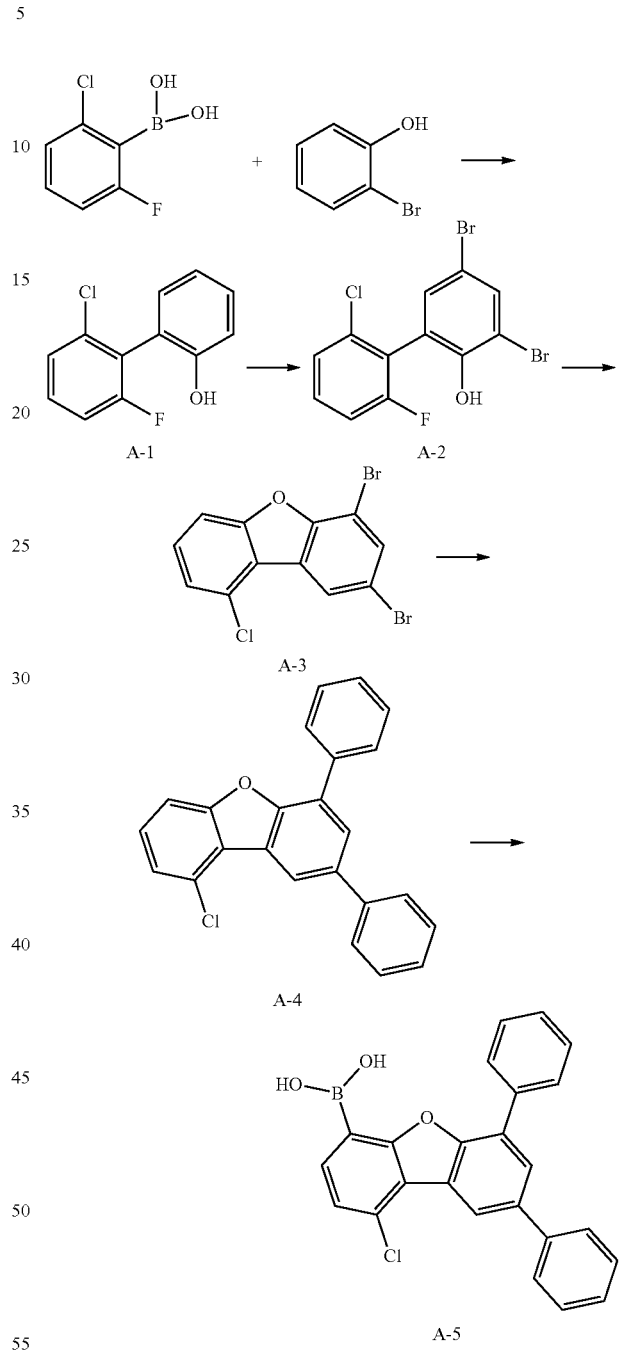

1) Synthesis of Compound A-1

2-Bromophenol(49.4 g, 287.3 mmol) and (2-chloro-6-fluorophenyl)boronic acid (50.0 g, 287.3 mmol) were dissolved in tetrahydrofuran (THF) (500 ml). A 2 M sodium carbonate (Na$_2$CO$_3$) solution (430 mL) and tetrakis(triphenylphosphine)-palladium(0) [Pd(PPh$_3$)$_4$] (10.0 g, 8.6 mmol) were introduced thereto, and the result was refluxed for 12 hours. After the reaction was finished, the result was cooled to room temperature, and a produced mixture was extracted three times using water and toluene. The toluene layer was separated, dried with magnesium sulfate and filtered, and a mixture obtained by vacuum distilling the filtrate was purified through column chromatography using chloroform and hexane to obtain Compound A-1 (34.4 g, yield 54%; MS: [M+H]$^+$=223).

2) Synthesis of Compound A-2

Compound A-1 (30 g, 135.1 mmol) was dissolved in chloroform (300 ml). N-bromosuccinimide (160.3 g, 270.25 mmol) was introduced thereto, and the result was stirred for 4 hours at room temperature. After the reaction was finished, water was added thereto. The layers were separated, and after stirring twice using a sodium thiosulfate solution, the layers were separated. After that, the result was distilled to obtain Compound A-2 (51.1 g, yield 100%; MS: [M+H]$^+$=379).

3) Synthesis of Compound A-3

Compound A-2 (51.1 g, 135.1 mmol) was dissolved in distilled dimethylformamide (DMF) (400 ml). This was cooled to 0° C., and sodium hydride (3.5 g, 145.9 mmol) was slowly added dropwise thereto. The result was stirred for 20 minutes, and then stirred for 1 hour at 100° C. After the reaction was finished, the result was cooled to room temperature, and ethanol (100 ml) was slowly introduced thereto. A mixture obtained by vacuum distilling the above-mentioned mixture was recrystallized with chloroform and ethyl acetate to obtain Compound A-3 (32.9 g, yield 68%; MS: [M+H]$^+$=359).

4) Synthesis of Compound A-4

Compound A-3 (32.9 g, 91.9 mmol) and phenylboronic acid (24.7 g, 202.3 mmol) were dissolved in tetrahydrofuran (THF) (300 ml). A 2 M potassium carbonate (K$_2$CO$_3$) solution (140 mL) and tetrakis(triphenylphosphine)palladium(0) [Pd(PPh$_3$)$_4$](2.1 g, 2 mol %) were introduced thereto, and the result was refluxed for 6 hours. After the reaction was finished, the result was cooled to room temperature, and a produced mixture was extracted three times using water and toluene. The toluene layer was separated, dried with magnesium sulfate and filtered, and a mixture obtained by vacuum distilling the filtrate was recrystallized using chloroform and ethyl acetate to obtain Compound A-4 (20.8 g, yield 64%; MS: [M+H]$^+$=355).

5) Synthesis of Compound A-5

After dissolving Compound A-4 (20.8 g, 58.7 mmol) in tetrahydrofuran (500 ml), the temperature was lowered to −78° C., and 1.7 M tertiary-butyllithium (t-BuLi) (41.5 ml, 70.5 mmol) was slowly added thereto. After raising the temperature to room temperature, the result was stirred for 3 hours, the temperature was lowered again to −78° C., triisopropyl borate (B(OiPr)$_3$) (13.3 ml, 70.5 mmol) was added thereto, and the result was stirred for 3 hours while slowing raising the temperature to room temperature. To the reaction mixture, a 2 N aqueous hydrochloric acid solution (200 ml) was added, and the result was stirred for 1.5 hours at room temperature. Produced precipitates were filtered, washed consecutively with water and ethyl ether, and then vacuum dried. After the drying, the precipitates were dispersed into ethyl ether, and, after stirring for 2 hours, filtered and dried to prepare Compound A-5 (16.1 g, yield 69%; MS: [M+H]$^+$=399).

<Synthesis Example 2>—Preparation of Subs 1 to 3

1) Synthesis of Compound Sub 1

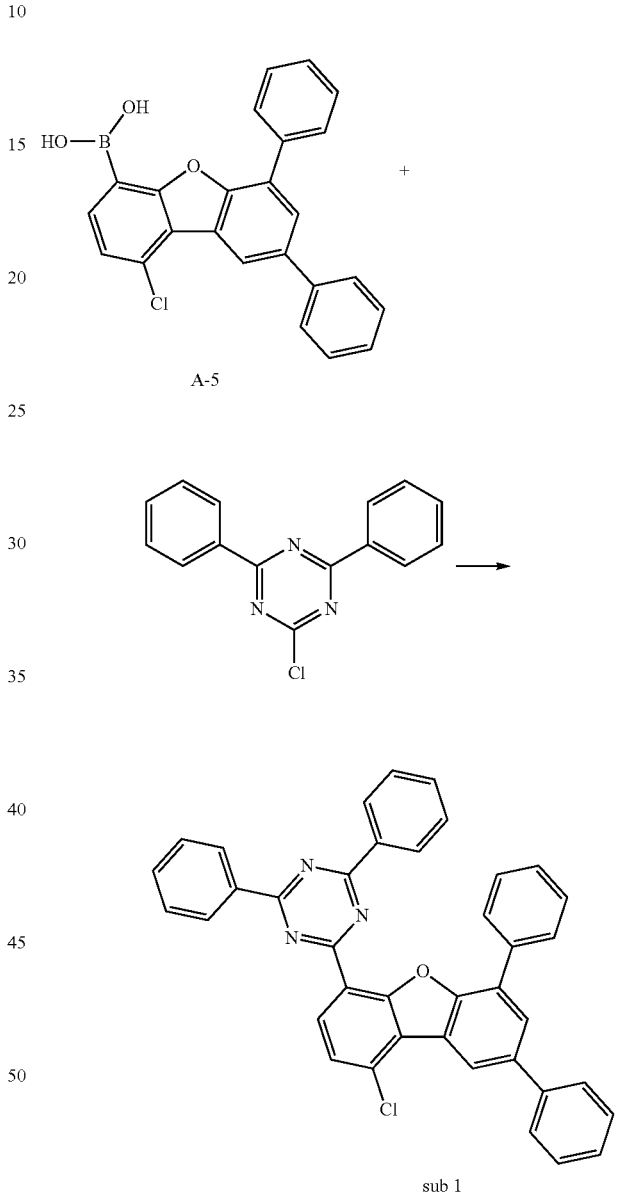

After dispersing Compound A-5 (15.0 g, 37.7 mmol) and 2-chloro-4,6-diphenyl-1,3,5-triazine (10.1 g, 37.7 mmol) into tetrahydrofuran (300 ml), a 2 M aqueous potassium carbonate solution (aq. K$_2$CO$_3$) (57 ml, 113 mmol) and then tetrakistriphenylphosphinopalladium [Pd(PPh$_3$)$_4$] (1.3 g, 3 mol %) were added thereto, and the result was stirred for 4 hours under reflux. The temperature was lowered to room temperature, and produced solids were filtered. The filtered solids were recrystallized with tetrahydrofuran and ethyl acetate, filtered, and then dried to prepare Compound sub 1 (15.4 g, yield 70%; MS: [M+H]$^+$=586).

1) Synthesis of Compound Sub 2

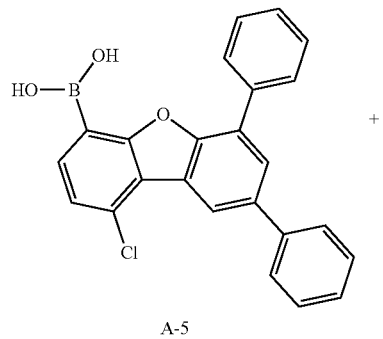

A-5

2) Synthesis of Compound Sub 3

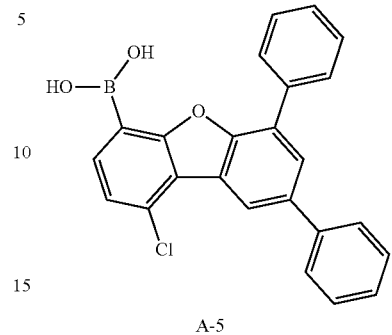

A-5

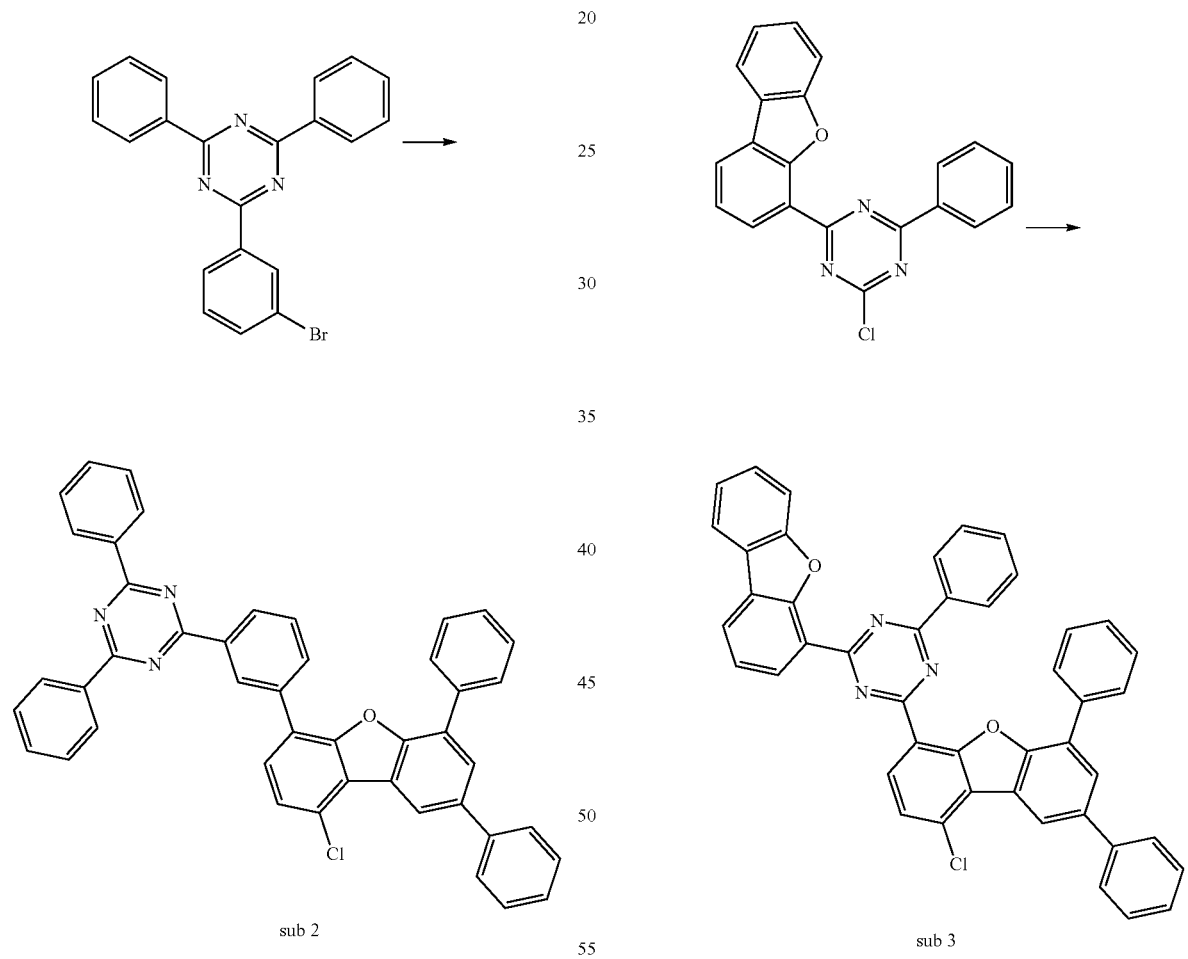

sub 2 sub 3

After dispersing Compound A-5 (15.0 g, 37.7 mmol) and 2-(3-bromophenyl)-4,6-diphenyl-1,3,5-triazine (14.6 g, 37.7 mmol) into tetrahydrofuran (300 ml), a 2 M aqueous potassium carbonate solution (aq. $K_2CO_3$) (57 ml, 113 mmol) and then tetrakistriphenylphosphinopalladium [$Pd(PPh_3)_4$] (1.3 g, 3 mol %) were added thereto, and the result was stirred for 4 hours under reflux. The temperature was lowered to room temperature, and produced solids were filtered. The filtered solids were recrystallized with tetrahydrofuran and ethyl acetate, filtered, and then dried to prepare Compound sub 2 (20.2 g, yield 81%; MS: $[M+H]^+$=662).

After dispersing Compound A-5 (15.0 g, 37.7 mmol) and 2-chloro-4-(dibenzo[b,d]furan-4-yl)-6-phenyl-1,3,5-triazine (13.5 g, 37.7 mmol) into tetrahydrofuran (300 ml), a 2 M aqueous potassium carbonate solution (aq. $K_2CO_3$) (57 ml, 113 mmol) and then tetrakistriphenylphosphinopalladium [$Pd(PPh_3)_4$] (1.3 g, 3 mol %) were added thereto, and the result was stirred for 4 hours under reflux. The temperature was lowered to room temperature, and produced solids were filtered. The filtered solids were recrystallized with tetrahydrofuran and ethyl acetate, filtered, and then dried to prepare Compound sub 3 (16.3 g, yield 66%; MS: $[M+H]^+$=658).

\<Synthesis Example 3\>—Preparation of Compounds 1 to 9

1) Synthesis of Compound 1

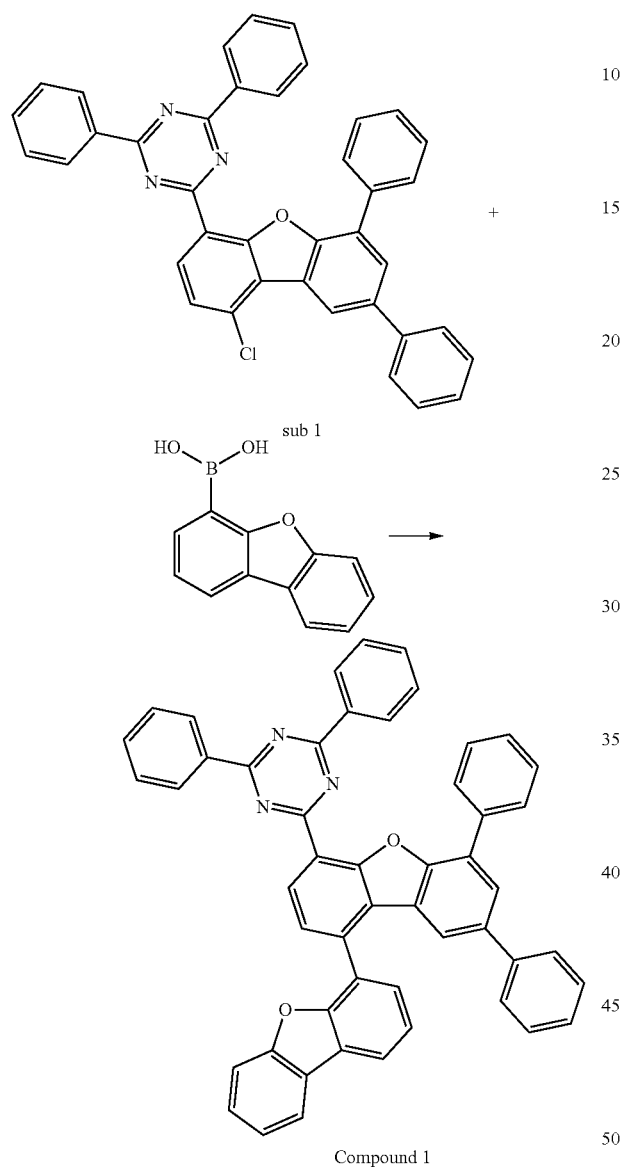

Compound 1

Under the nitrogen atmosphere, Compound sub 1 (10 g, 17.1 mmol) and dibenzo[b,d]furan-4-ylboronic acid (4.5 g, 70.5 mmol) were introduced to dioxane (150 ml), and the mixture was stirred and refluxed. After that, potassium phosphate (10.9 g, 51.3 mmol) dissolved in water (30 ml) was introduced thereto, and after sufficiently stirring the result, bis(dibenzylidineacetone)palladium (0.3 g, 0.5 mmol) and tricyclohexylphosphine (0.3 g, 1.0 mmol) were introduced thereto. After reacting for 8 hours, the temperature was lowered to room temperature, and the result was filtered. The filtered material was extracted with chloroform and water, and then the organic layer was dried using magnesium sulfate. After that, the organic layer was vacuum distilled and recrystallized using ethyl acetate. Produced solids were filtered and then dried to prepare Compound 1 (5.5 g, 45%, MS: [M+H]+=718).

2) Synthesis of Compound 2

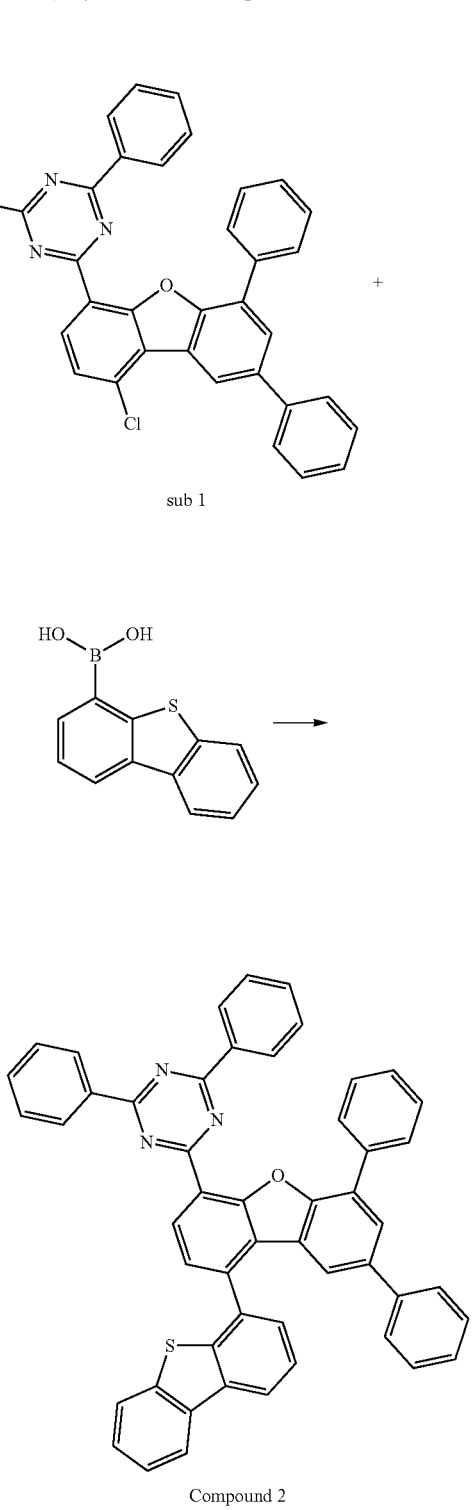

Compound 2

Compound 2 (8.8 g, 70%, MS: [M+H]+=734) was prepared in the same manner as in the method for preparing Compound 1 except that dibenzo[b,d]thiophen-4-ylboronic acid was used in the reaction instead of dibenzo[b,d]furan-4-ylboronic acid as in the above-described reaction formula.

3) Synthesis of Compound 3

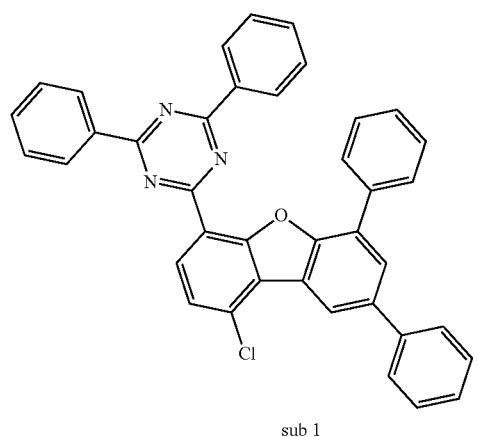

sub 1

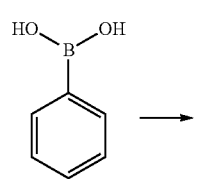

Compound 3

Compound 3 (5.5 g, 51%, MS: [M+H]+=628) was prepared in the same manner as in the method for preparing Compound 1 except that phenylboronic acid was used in the reaction instead of dibenzo[b,d]furan-4-ylboronic acid as in the above-described reaction formula.

4) Synthesis of Compound 4

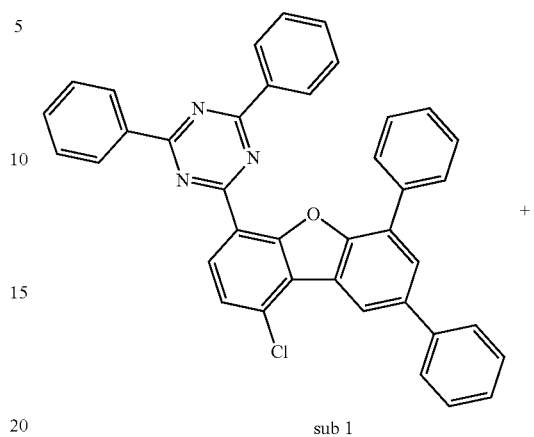

sub 1

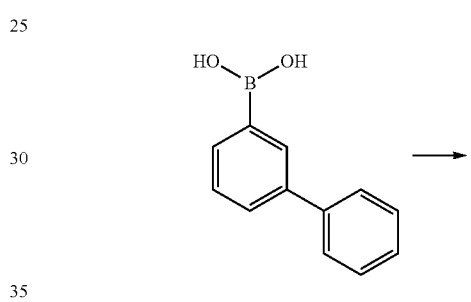

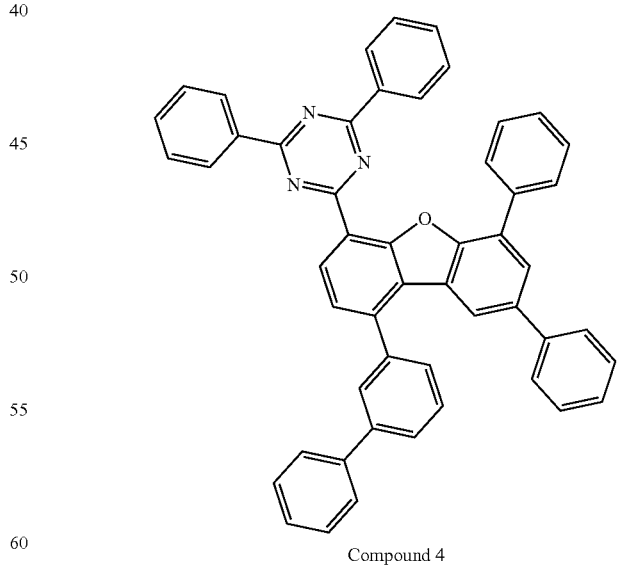

Compound 4

Compound 4 (5.2 g, 43%, MS: [M+H]+=704) was prepared in the same manner as in the method for preparing Compound 1 except that [1,1'-biphenyl]-3-ylboronic acid was used in the reaction instead of dibenzo[b,d]furan-4-ylboronic acid as in the above-described reaction formula.

5) Synthesis of Compound 5

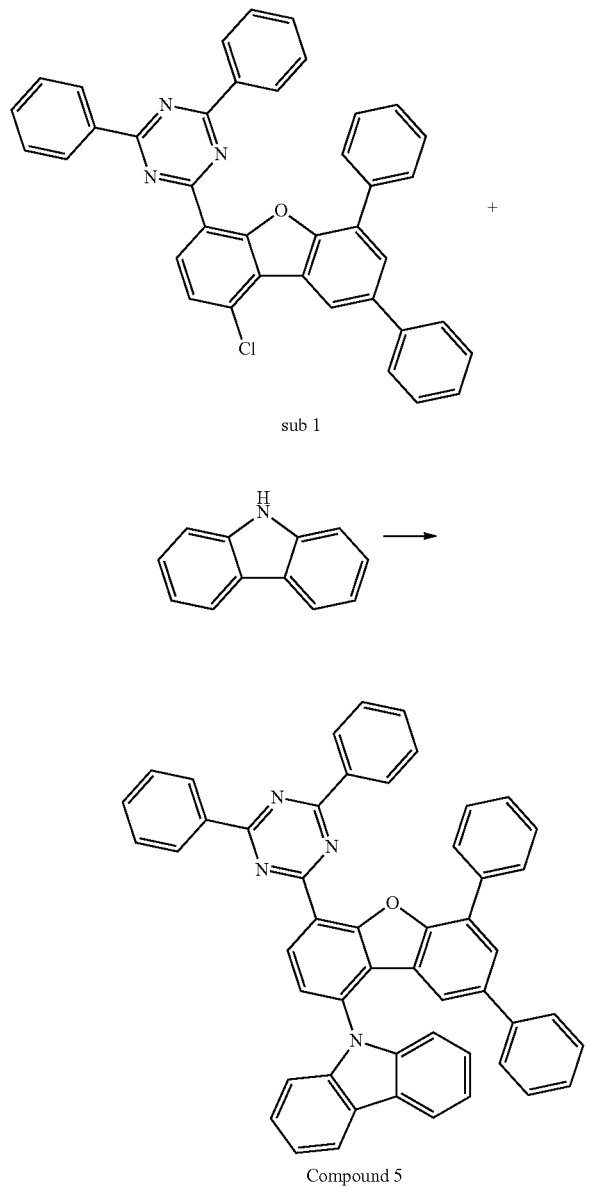

Compound 5

6) Synthesis of Compound 6

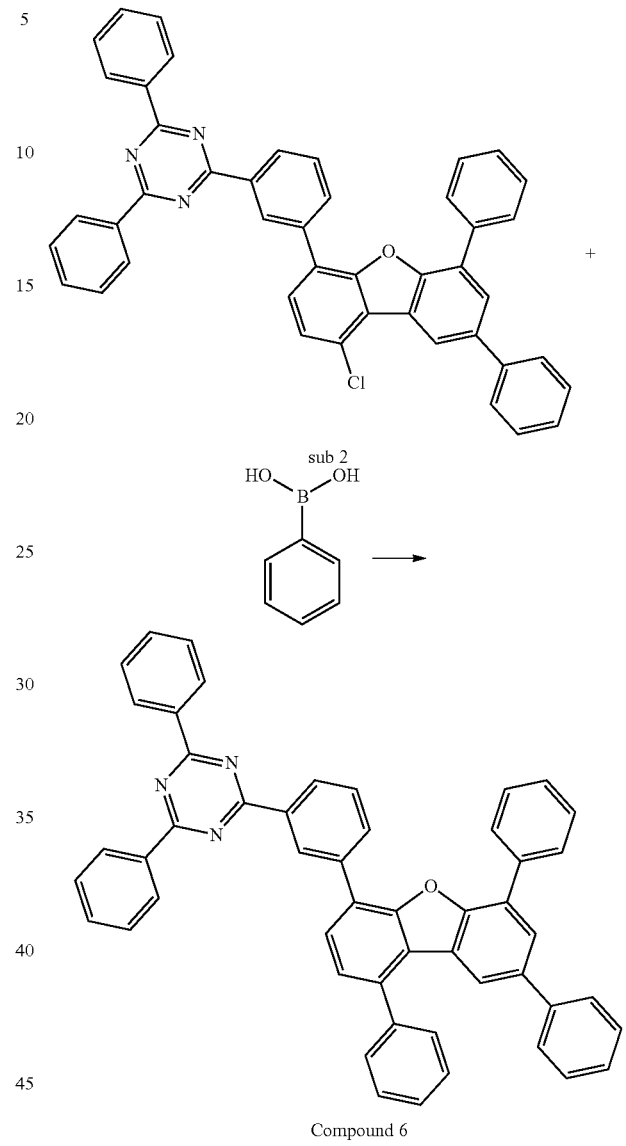

Compound 6

Under the nitrogen atmosphere, Compound sub 1 (10 g, 17.1 mmol) and 9H-carbazole (2.9 g, 17 mmol) were dissolved by introducing xylene (100 mL), and after adding sodium tertiary-butoxide (3.3 g, 34.1 mmol) thereto, the temperature was raised. Bis(tri-tertiary-butylphosphine)palladium (0.3 g, 3 mol %) was introduced thereto, and the result was stirred for 4 hours under reflux. When the reaction was completed, the temperature was lowered to room temperature, and produced solids were filtered. The solids were dissolved in chloroform, and washed twice with water. The organic layer was separated, and after adding anhydrous magnesium sulfate thereto, the organic layer was stirred and then filtered, and the filtrate was vacuum distilled. The concentrated compound was purified through a silica column using ethyl acetate and hexane to prepare light yellow solid Compound 5 (7.1 g, 58%, MS: [M+H]$^+$=717).

Under the nitrogen atmosphere, Compound sub 2 (10 g, 15.1 mmol) and phenylboronic acid (4.2 g, 16.6 mmol) were introduced to dioxane (150 ml), and the mixture was stirred and refluxed. After that, potassium phosphate (10.9 g, 51.3 mmol) dissolved in water (30 ml) was introduced thereto, and after sufficiently stirring the result, bis(dibenzylidineacetone)palladium (0.3 g, 0.5 mmol) and tricyclohexylphosphine (0.3 g, 1.0 mmol) were introduced thereto. After reacting for 8 hours, the temperature was lowered to room temperature, and the result was filtered. The filtered material was extracted with chloroform and water, and then the organic layer was dried using magnesium sulfate. After that, the organic layer was vacuum distilled and recrystallized using ethyl acetate. Produced solids were filtered and then dried to prepare Compound 6 (7.5 g, 71%, MS: [M+H]+= 704).

7) Synthesis of Compound 7

8) Synthesis of Compound 8

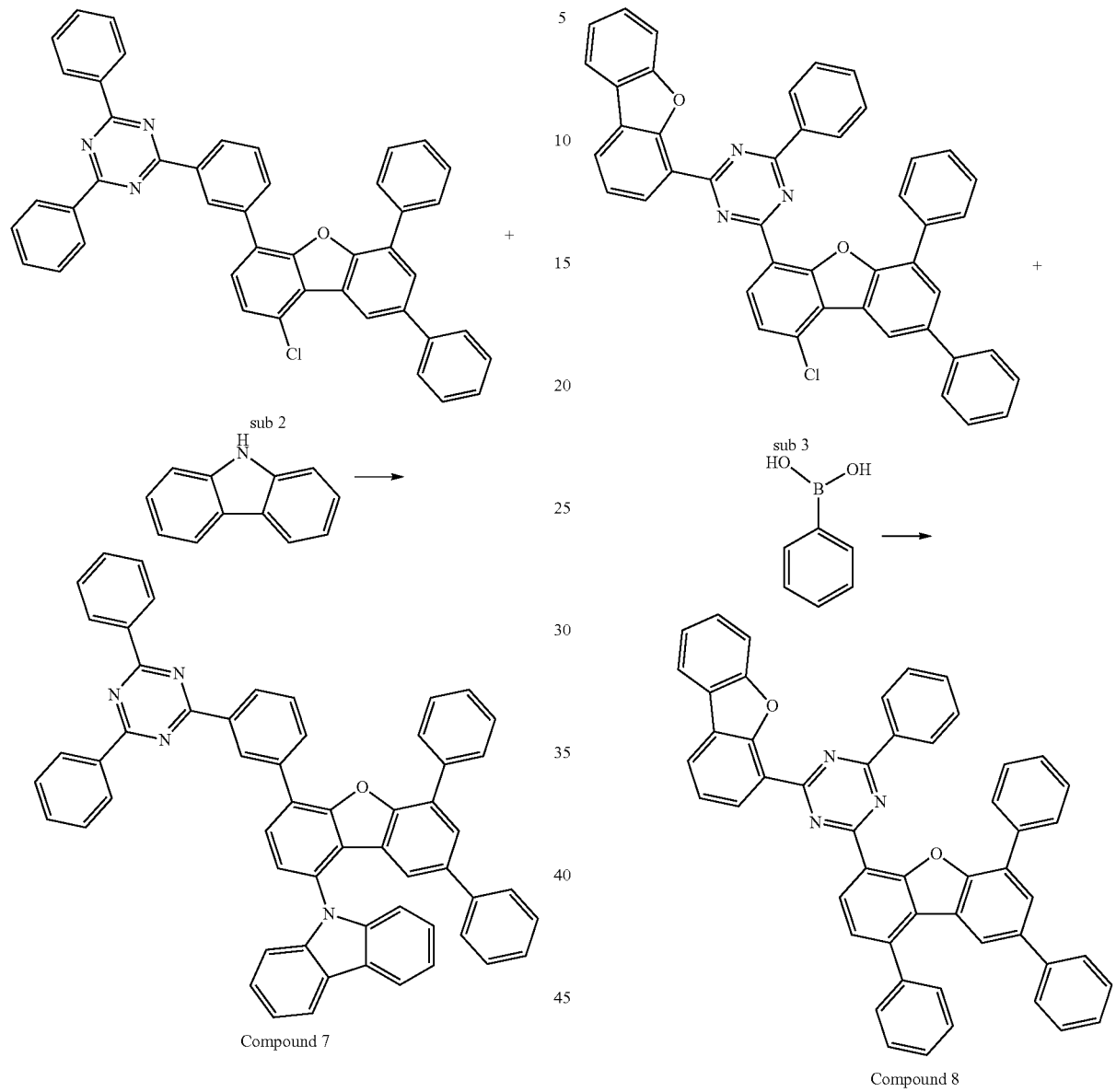

Compound 7

Compound 8

Under the nitrogen atmosphere, Compound sub 2 (10 g, 15.1 mmol) and 9H-carbazole (2.5 g, 15.1 mmol) were dissolved by introducing xylene (100 mL), and after adding sodium tertiary-butoxide (2.9 g, 34.1 mmol) thereto, the temperature was raised. Bis(tri-tertiary-butylphosphine)palladium (0.2 g, 3 mol %) was introduced thereto, and the result was stirred for 4 hours under reflux. When the reaction was completed, the temperature was lowered to room temperature, and produced solids were filtered. The solids were dissolved in chloroform, and washed twice with water. The organic layer was separated, and after adding anhydrous magnesium sulfate thereto, the organic layer was stirred and then filtered, and the filtrate was vacuum distilled. The concentrated compound was purified through a silica column using ethyl acetate and hexane to prepare light yellow solid Compound 7 (6.1 g, 51%, MS: [M+H]$^+$=793).

Under the nitrogen atmosphere, Compound sub 3 (10 g, 14.8 mmol) and phenylboronic acid (2.0 g, 16.3 mmol) were introduced to dioxane (150 ml), and the mixture was stirred and refluxed. After that, potassium phosphate (6.3 g, 29.6 mmol) dissolved in water (30 ml) was introduced thereto, and after sufficiently stirring the result, bis(dibenzylidine-acetone)palladium (0.3 g, 0.5 mmol) and tricyclohexylphosphine (0.3 g, 1.0 mmol) were introduced thereto. After reacting for 8 hours, the temperature was lowered to room temperature, and the result was filtered. The filtered material was extracted with chloroform and water, and then the organic layer was dried using magnesium sulfate. After that, the organic layer was vacuum distilled and recrystallized using ethyl acetate. Produced solids were filtered and then dried to prepare Compound 8 (6.9 g, 65%, MS: [M+H]+= 718).

9) Synthesis of Compound 9

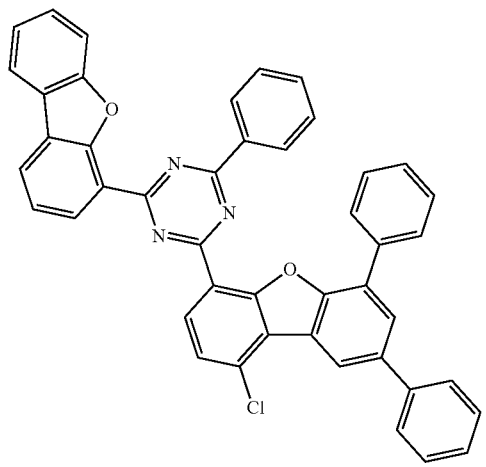

sub 3
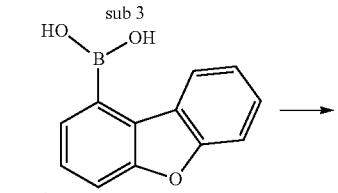

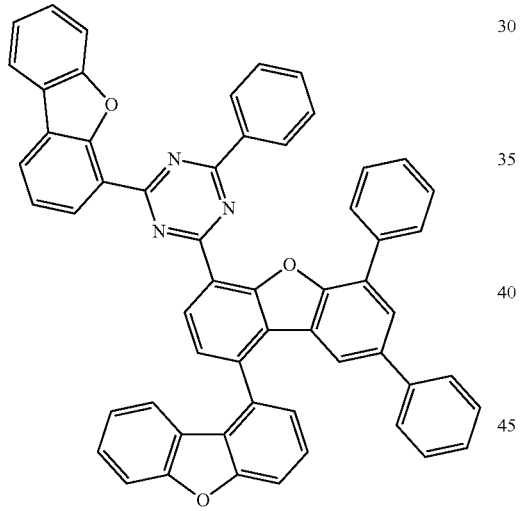

Compound 9

Compound 9 (3.9 g, 33%, MS: [M+H]+=808) was prepared in the same manner as in the method for preparing Compound 8 except that dibenzo[b,d]furan-1-ylboronic acid was used in the reaction instead of phenylboronic acid as in the above-described reaction formula.

Experimental Examples

Experimental Example 1

A glass substrate on which indium tin oxide (ITO) was coated as a thin film to a thickness of 1,300 Å was placed in detergent-dissolved distilled water and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, a hole injection layer was formed by thermal vacuum depositing the following HI-1 compound to a thickness of 50 Å. On the hole injection layer, a hole transfer layer was formed by thermal vacuum depositing the following HT-1 compound to a thickness of 250 Å, and on the HT-1 deposited film, an electron blocking layer was formed by vacuum depositing the following HT-2 compound to a thickness of 50 Å. On the HT-2 deposited film, Compound 1, the following YGH-1 compound and phosphorescent dopant YGD-1 were co-deposited in a weight ratio of 44:44:12 to form a light emitting layer having a thickness of 400 Å. An electron transfer layer was formed on the light emitting layer by vacuum depositing the following ET-1 compound to a thickness of 250 Å, and on the electron transfer layer, an electron injection layer having a thickness of 100 Å was formed by vacuum depositing the following ET-2 compound and Li in a weight ratio of 98:2. A cathode was formed on the electron injection layer by depositing aluminum to a thickness of 1000 Å.

HI-1
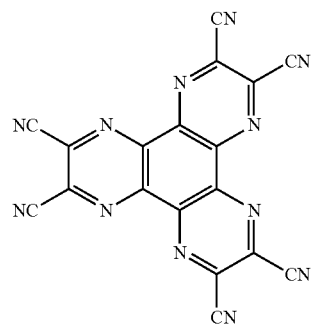

HT-1
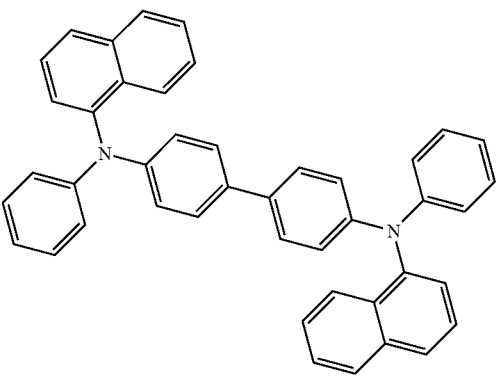

HT-2

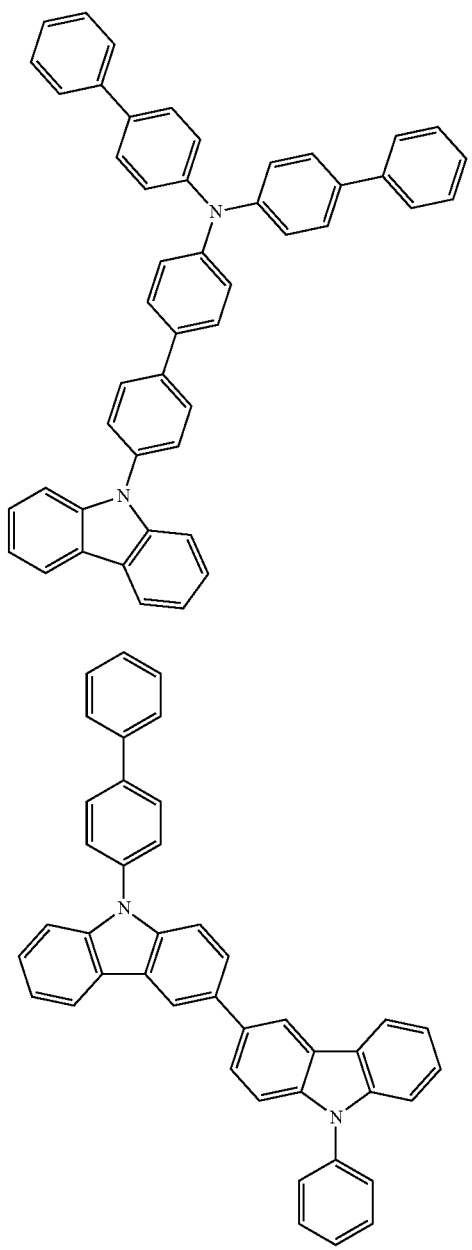

YGH-1

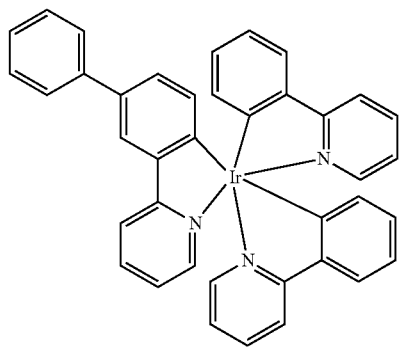

YGD-1

ET-1

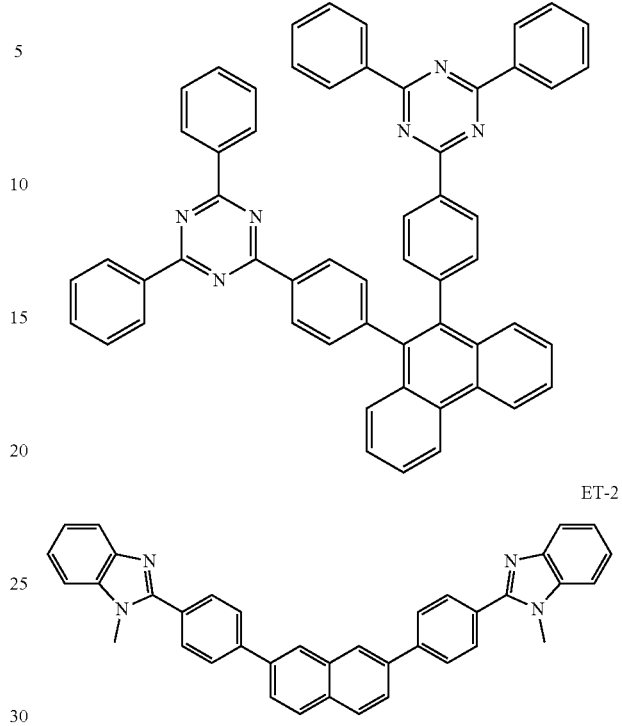

ET-2

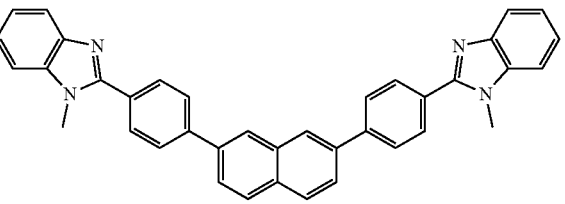

In the above-mentioned process, the deposition rates of the organic materials were maintained at 0.4 Å/sec to 0.7 Å/sec, the deposition rate of the aluminum was maintained at 2 Å/sec, and the degree of vacuum during the deposition was maintained at $1 \times 10^{-7}$ torr to $5 \times 10^{-8}$ torr.

Experimental Examples 2 to 9

Organic light emitting devices were manufactured in the same manner as in Experimental Example 1 except that compounds described in the following Table 1 were used instead of Compound 1 in Experimental Example 1.

Comparative Experimental Examples 1 to 3

Organic light emitting devices were manufactured in the same manner as in Experimental Example 1 except that compounds described in the following Table 1 were used instead of Compound 1 in Experimental Example 1. Compounds of CE1 to CE3 of the following Table 1 are as follows.

CE1

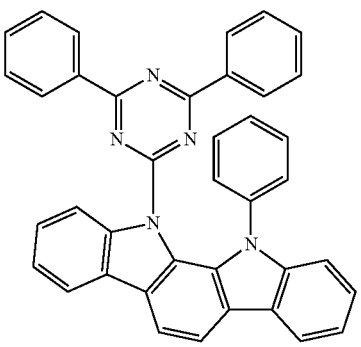

-continued

CE2

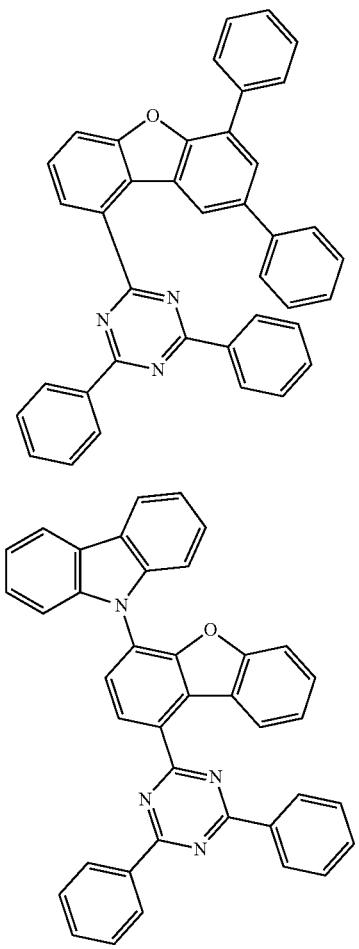

CE3

For the organic light emitting devices manufactured in the experimental examples and the comparative experimental examples, voltage and efficiency were measured at current density of 10 mA/cm², and a lifetime was measured at current density of 50 mA/cm². The results are shown in the following Table 1. Herein, LT95 means time taken for luminance becoming 95% with respect to initial luminance.

TABLE 1

| | Compound | Voltage (V) (@10 mA/cm²) | Efficiency (Cd/A) (@10 mA/cm²) | Color Co-ordinate (x, y) | Lifetime (h) (LT$_{95}$ at 50 mA/cm²) |
|---|---|---|---|---|---|
| Experimental Example 1 | Compound 1 | 3.8 | 83 | 0.45, 0.54 | 170 |
| Experimental Example 2 | Compound 2 | 3.9 | 82 | 0.46, 0.53 | 190 |
| Experimental Example 3 | Compound 3 | 3.9 | 85 | 0.45, 0.53 | 130 |
| Experimental Example 4 | Compound 4 | 3.9 | 84 | 0.45, 0.54 | 150 |
| Experimental Example 5 | Compound 5 | 4.1 | 82 | 0.45, 0.54 | 160 |
| Experimental Example 6 | Compound 6 | 3.9 | 84 | 0.45, 0.54 | 110 |
| Experimental Example 7 | Compound 7 | 4.0 | 82 | 0.46, 0.53 | 120 |
| Experimental Example 8 | Compound 8 | 4.0 | 81 | 0.45, 0.54 | 180 |
| Experimental Example 9 | Compound 9 | 4.3 | 80 | 0.45, 0.54 | 145 |
| Comparative Experimental Example 1 | CE1 | 4.5 | 70 | 0.46, 0.54 | 80 |
| Comparative Experimental Example 2 | CE2 | 4.0 | 84 | 0.45, 0.54 | 100 |
| Comparative Experimental Example 3 | CE3 | 4.5 | 70 | 0.45, 0.55 | 20 |

As shown in Table 1, it was identified that, when using the compound of the present disclosure as a light emitting layer material, properties of excellent efficiency and lifetime were obtained compared to Comparative Experimental Examples 1 to 3. This is considered to be due to the fact that electron stability increased by increasing substituting positions of the dibenzofuran substituents.

The invention claimed is:
1. A heterocyclic compound of Chemical Formula 1:

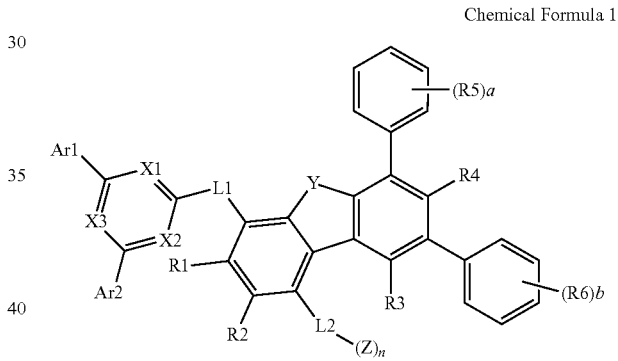

Chemical Formula 1 wherein, in Chemical Formula 1:
X1 to X3 are the same as or different from each other, and each independently is N or CH;
at least two or more of X1 to X3 are N;
Y is O or S;
R1 and R2 are the same as or different from each other, and each independently is hydrogen, deuterium, a halogen group, a nitrile group, an unsubstituted alkyl group, an unsubstituted aryl group, or a silyl group selected from the group consisting of a trimethylsilyl group, a triethylsilyl group, a t-butyldimethylsilyl group, a vinyldimethylsilyl group, a propyldimethylsilyl group, a triphenylsilyl group, a diphenylsilyl group, and a phenylsilyl group;
R3 to R6 are the same as or different from each other, and each independently is hydrogen, deuterium, a halogen group, a nitrile group, an unsubstituted alkyl group, a silyl group selected from the group consisting of a trimethylsilyl group, a triethylsilyl group, a t-butyldimethylsilyl group, a vinyldimethylsilyl group, a propyldimethylsilyl group, a triphenylsilyl group, a diphenylsilyl group, and a phenylsilyl group, an unsubstituted aryl group, or an unsubstituted heteroaryl group;

Ar1 and Ar2 are the same as or different from each other, and each independently is a phenyl group, a biphenyl group, a naphthyl group, a terphenyl group, a fluorene group, a spirobifluorene group, a phenanthrene group, a triphenylene group, a carbazole group, a dibenzofuran group, a dibenzothiophene group, a benzonaphthofuran group, or a benzonaphthothiophene group, and the phenyl group, the biphenyl group, the naphthyl group, the terphenyl group, the fluorene group, the spirobifluorene group, the phenanthrene group, the triphenylene group, the carbazole group, the dibenzofuran group, the dibenzothiophene group, the benzonaphthofuran group, or the benzonaphthothiophene group is unsubstituted or substituted with one or more substituents selected from the group consisting of deuterium, a halogen group, an alkyl group having 1 to 10 carbon atoms, an aryl group having 6 to 20 carbon atoms that is unsubstituted or substituted with an alkyl group having 1 to 10 carbon atoms, and a heteroaryl group having 3 to 30 carbon atoms that is unsubstituted or substituted with an aryl group having 6 to 30 carbon atoms;

L1 and L2 are the same as or different from each other, and each independently is a direct bond, a phenylene group that is unsubstituted or substituted with an alkyl group having 1 to 10 carbon atoms, a naphthylene group that is unsubstituted or substituted with an alkyl group having 1 to 10 carbon atoms, a divalent biphenyl group that is unsubstituted or substituted with an alkyl group having 1 to 10 carbon atoms, a divalent terphenyl group that is unsubstituted or substituted with an alkyl group having 1 to 10 carbon atoms, a divalent quaterphenyl group that is unsubstituted or substituted with an alkyl group having 1 to 10 carbon atoms, a divalent fluorene group that is unsubstituted or substituted with an alkyl group having 1 to 10 carbon atoms, a divalent anthracene group that is unsubstituted or substituted with an alkyl group having 1 to 10 carbon atoms, a divalent pyrene group that is unsubstituted or substituted with an alkyl group having 1 to 10 carbon atoms, a divalent triphenylene group that is unsubstituted or substituted with an alkyl group having 1 to 10 carbon atoms, or a divalent phenanthrene group that is unsubstituted or substituted with an alkyl group having 1 to 10 carbon atoms;

Z is a nitrile group, a halogen group, an unsubstituted alkyl group having 1 to 10 carbon atoms, a silyl group that is unsubstituted or substituted with an alkyl group having 1 to 10 carbon atoms, an unsubstituted aryl group, or an unsubstituted heteroaryl group selected from the group consisting of a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, or a dibenzofuranyl group;

n is an integer of 1 to 2;

when n is 2, the Zs are the same as or different from each other; and a and b are an integer of 0 to 5, and when a and b are a plural number, the substituents in the parentheses are the same as or different from each other.

2. The heterocyclic compound of claim 1, wherein Ar1 and Ar2 are the same as or different from each other, and each independently is a phenyl group; a biphenyl group; a terphenyl group; a naphthyl group; a phenanthrene group; a carbazole group that is unsubstituted or substituted with a phenyl group; a dibenzofuran group; or a dibenzothiophene group.

3. The heterocyclic compound of claim 1, wherein L1 and L2 are the same as or different from each other, and each independently is a direct bond, an unsubstituted phenylene group, an unsubstituted naphthylene group, or an unsubstituted divalent biphenyl group.

4. The heterocyclic compound of claim 1, wherein Z is a nitrile group, a halogen group, an unsubstituted alkyl group having 1 to 10 carbon atoms, a trimethylsilyl group, a phenyl group, a naphthyl group; a biphenyl group, a terphenyl group, a phenanthrene group, a triphenylene group, a pyridine group; a dibenzofuran group; a dibenzothiophene group; a 9-phenylcarbazole group; or a quinoline group.

5. The heterocyclic compound of claim 1, wherein the compound of Chemical Formula 1 is any one compound selected from among the following compounds:

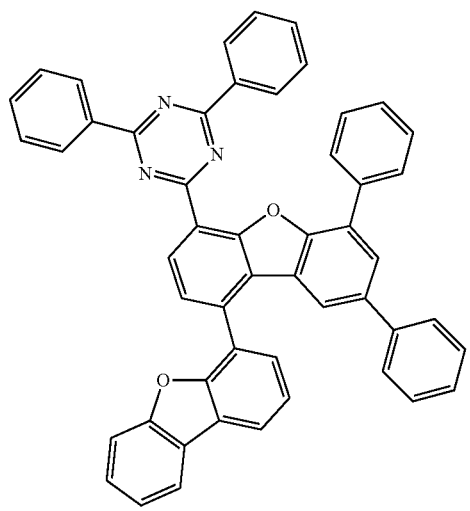

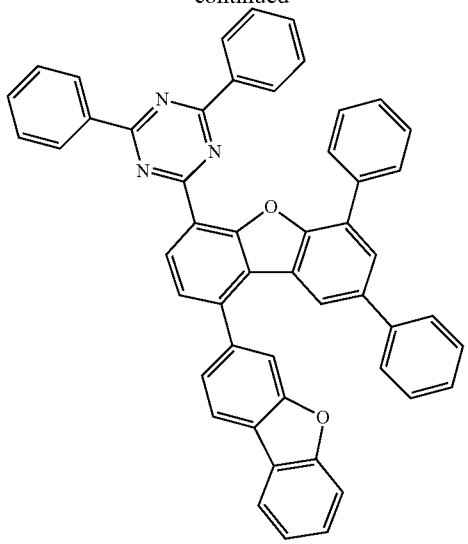
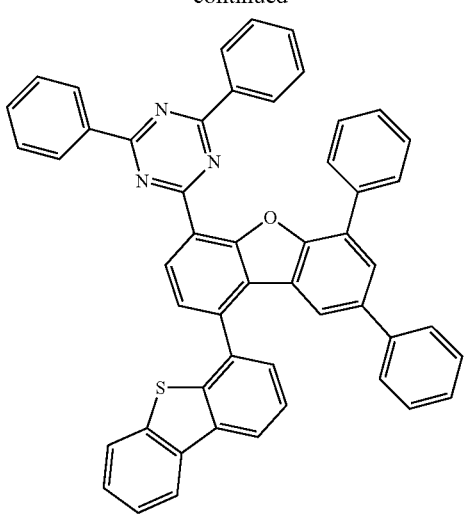
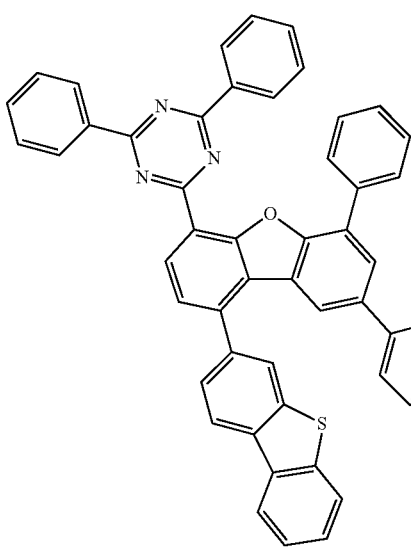
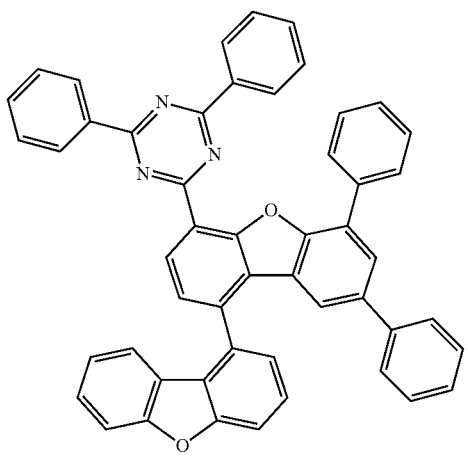
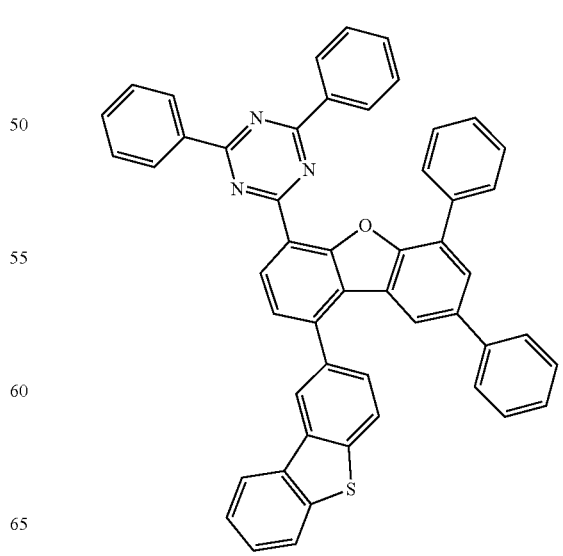

-continued
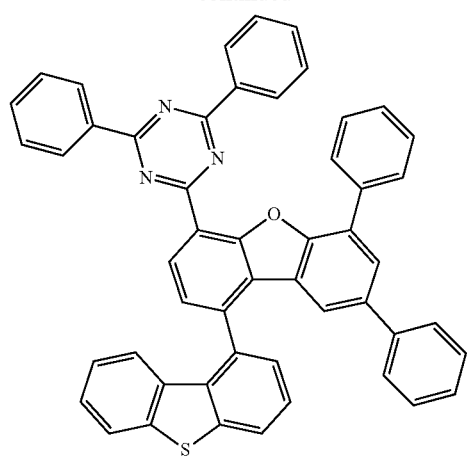
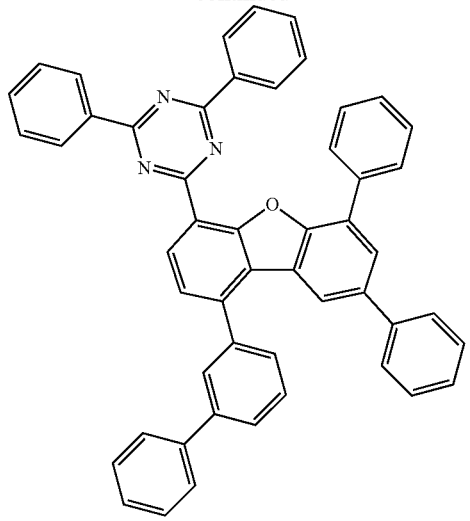
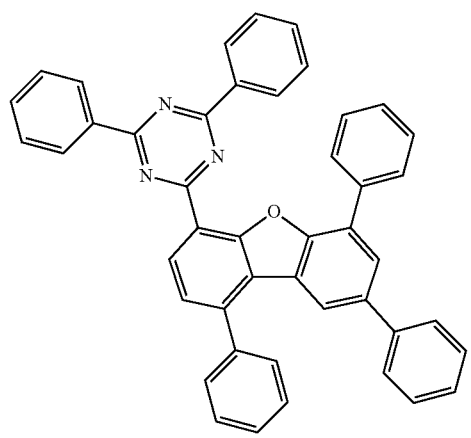
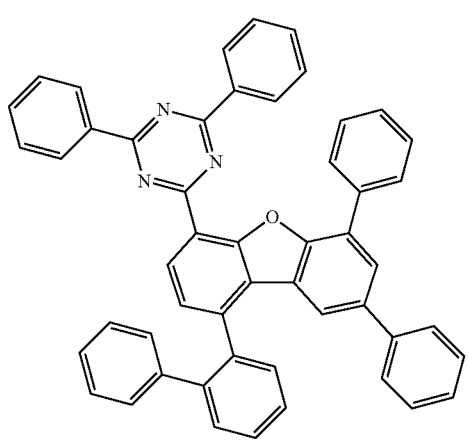
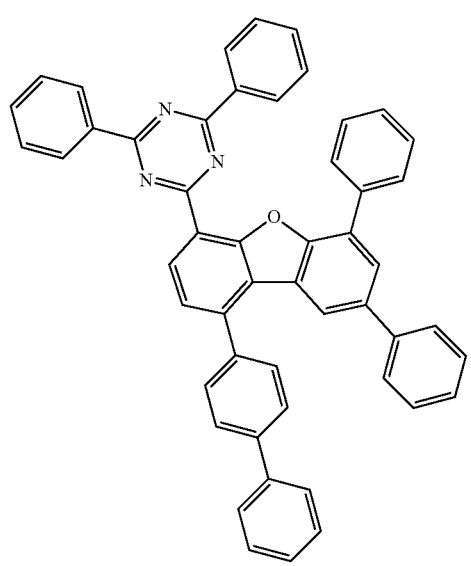
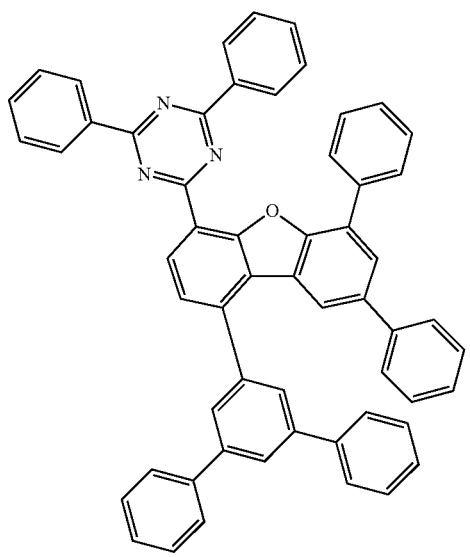

-continued
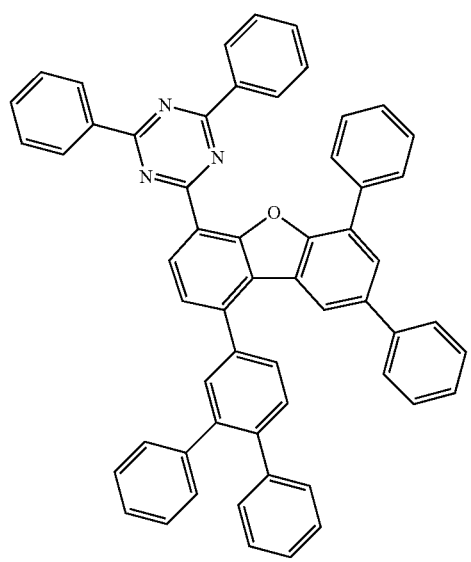
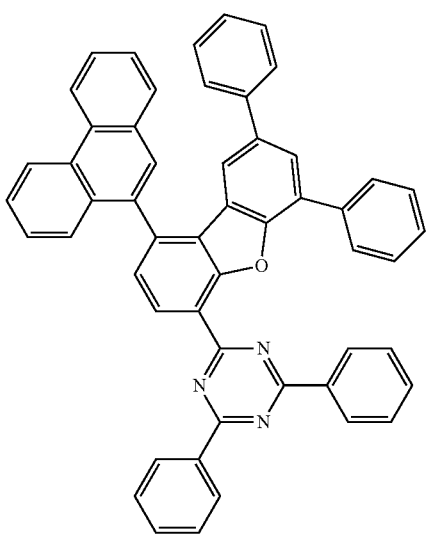
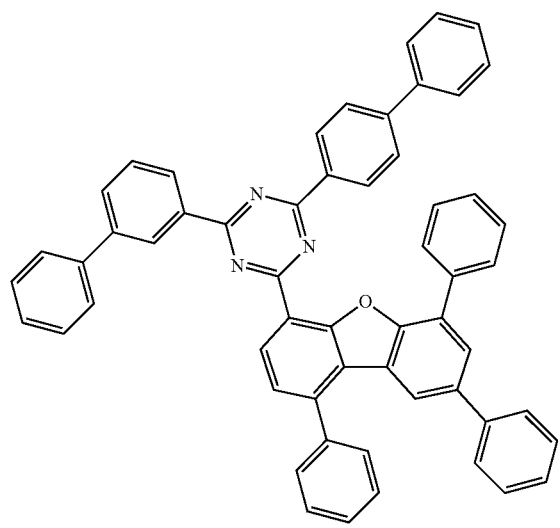
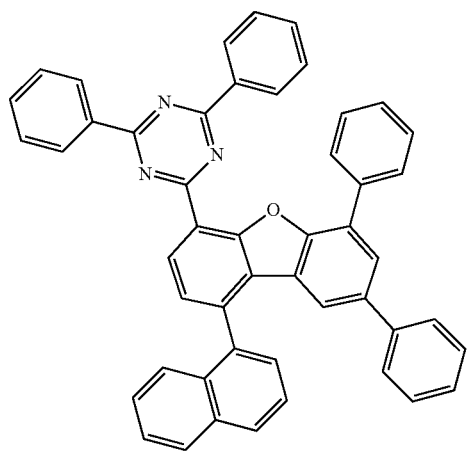
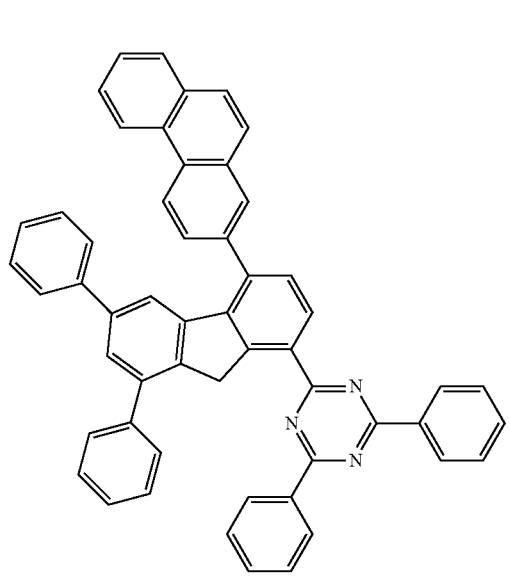
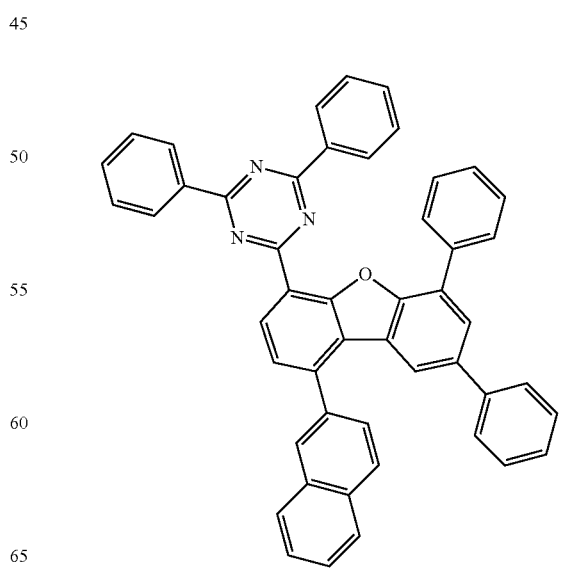

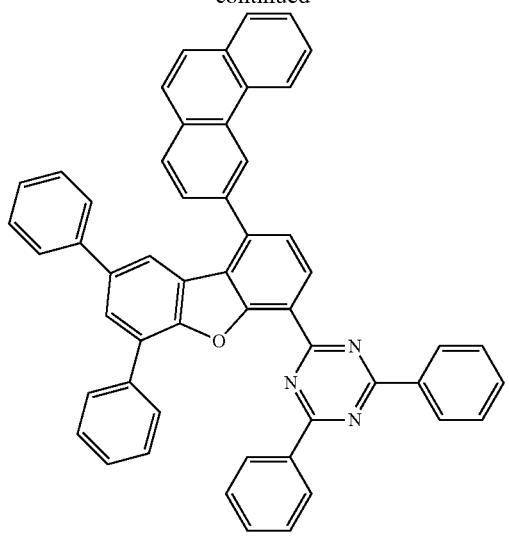
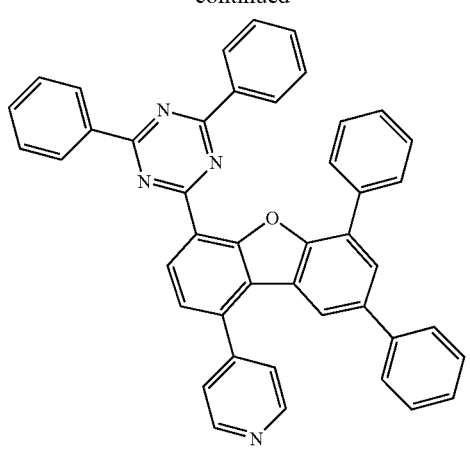
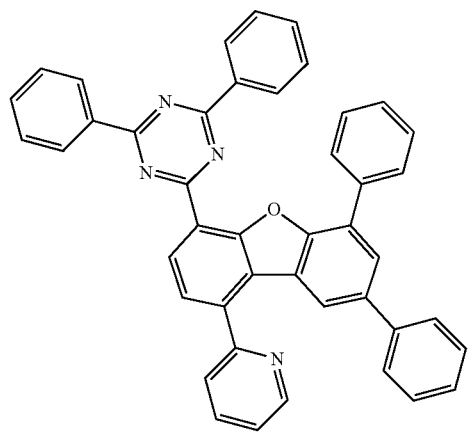
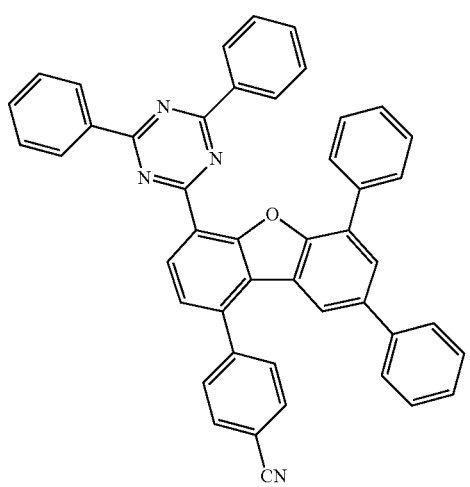
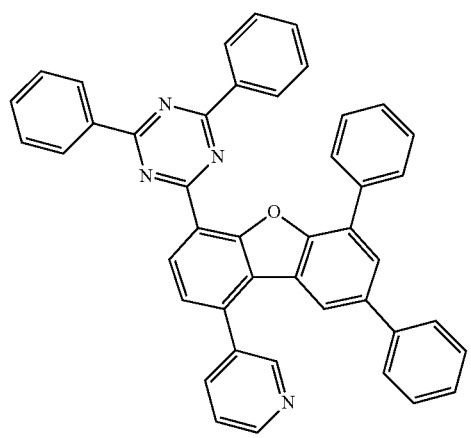
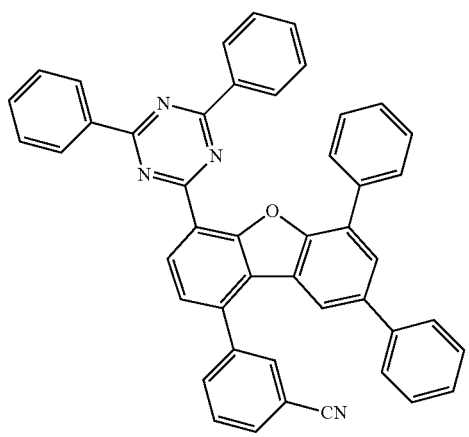

-continued
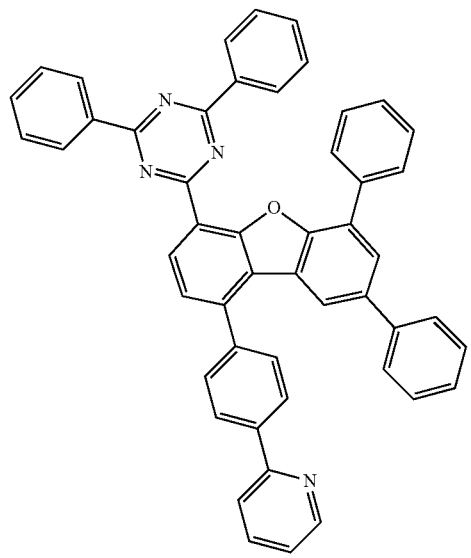
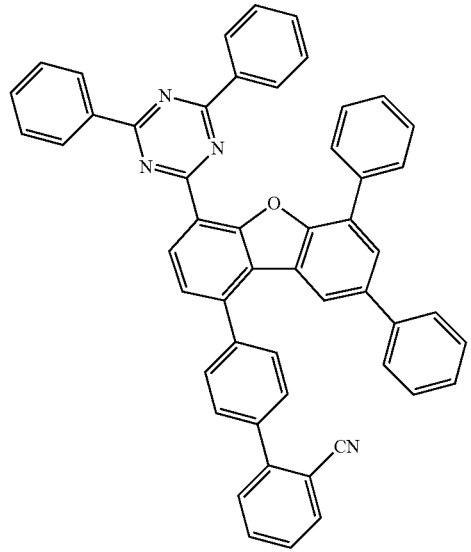
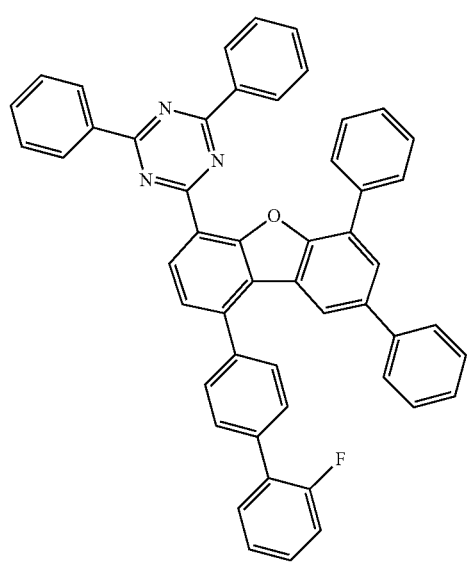
-continued
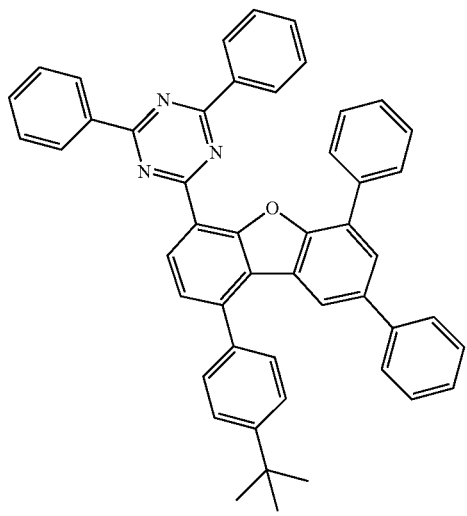
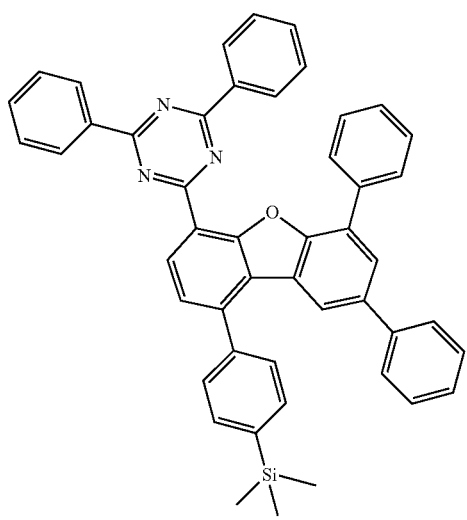
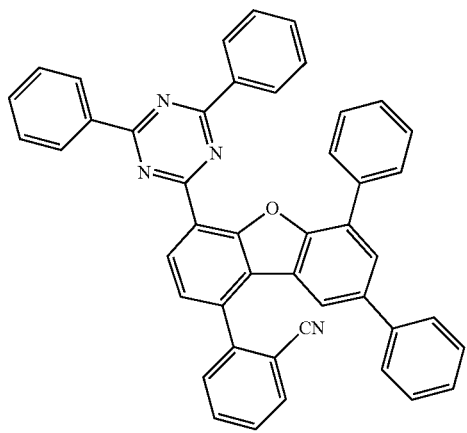

71
-continued

72
-continued

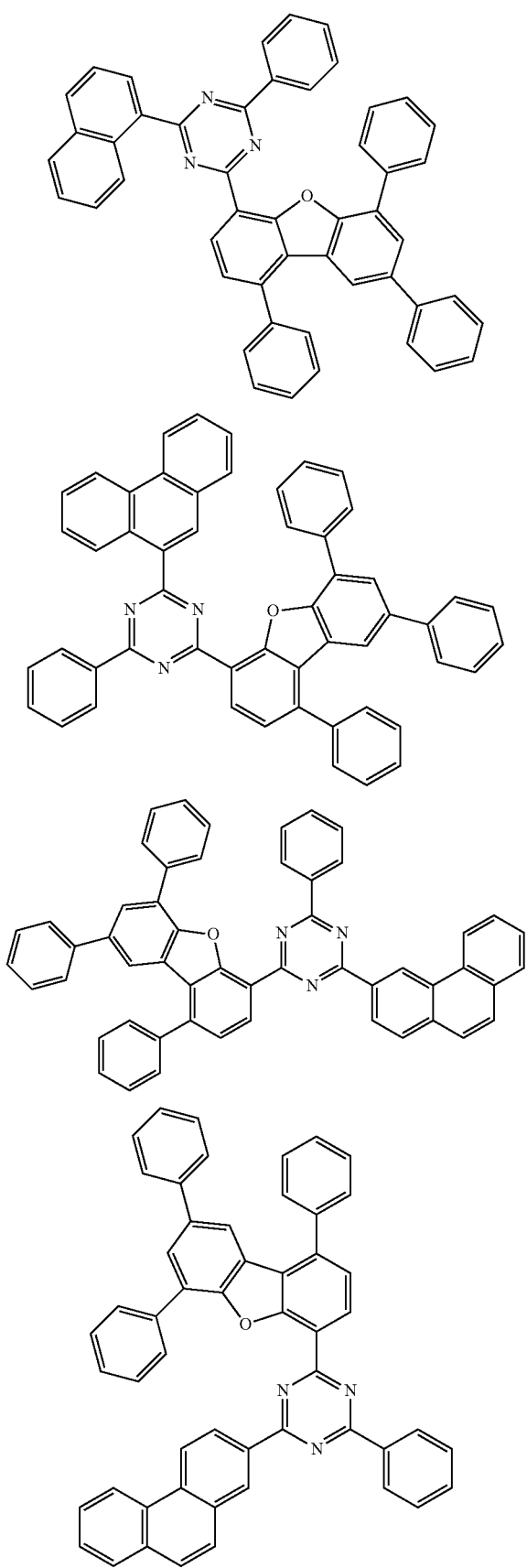
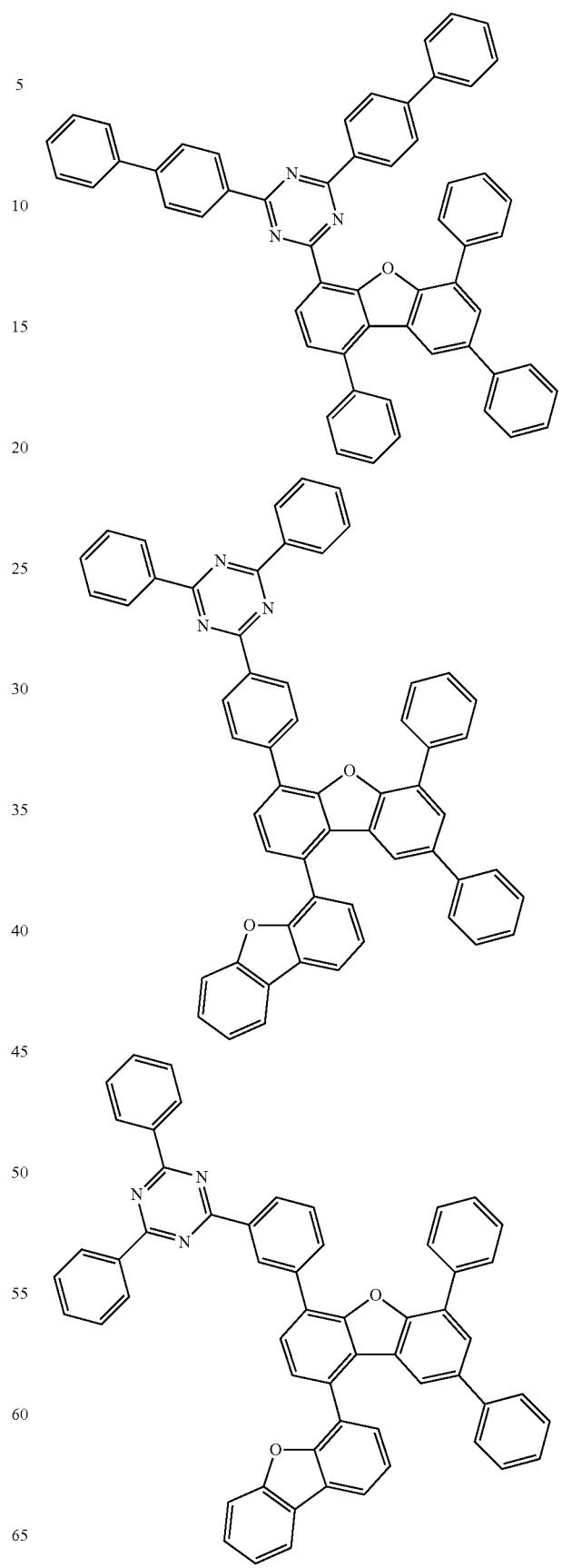

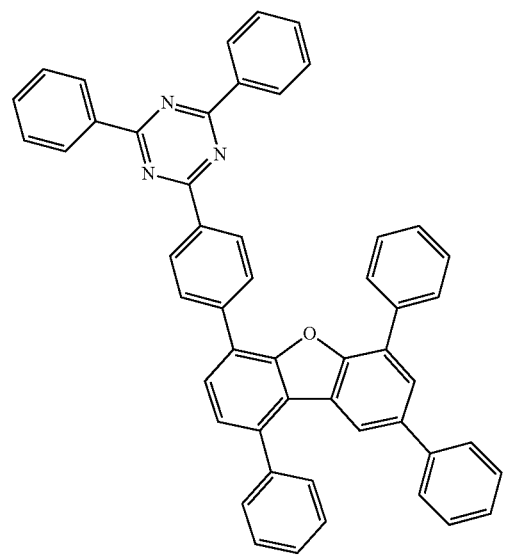
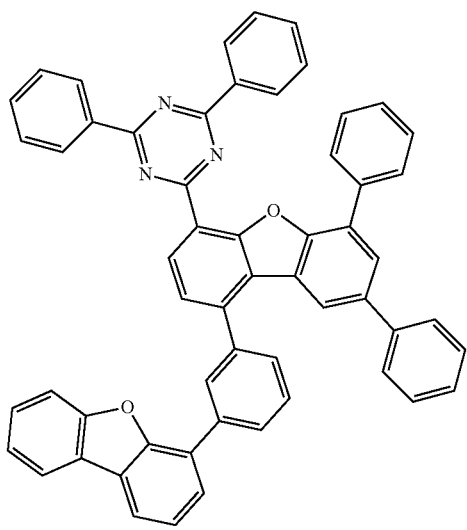
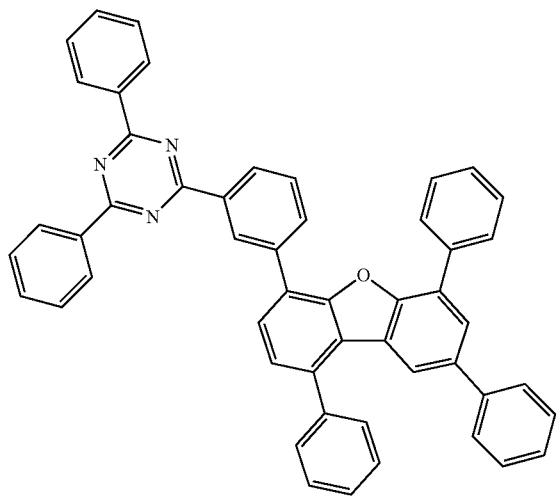
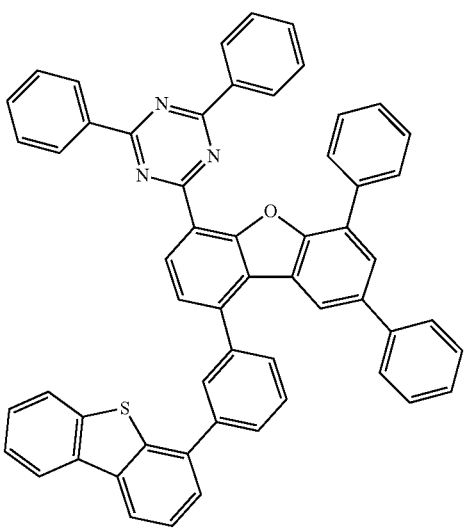
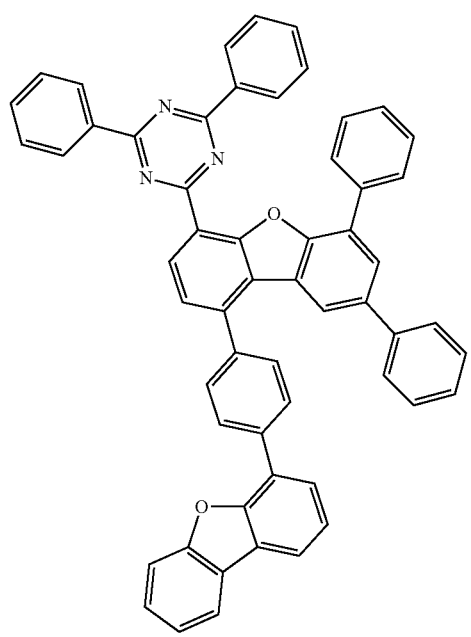
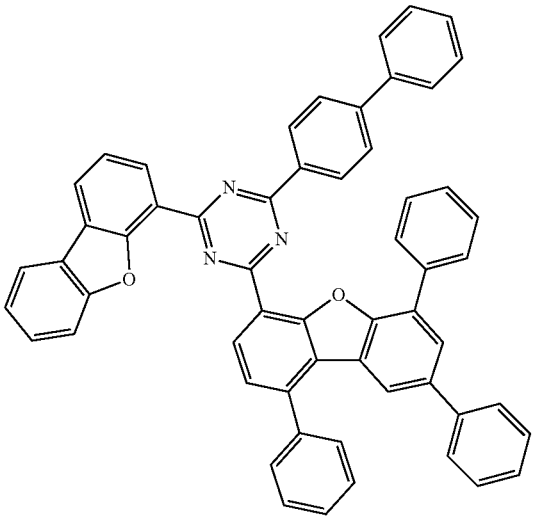

77
-continued
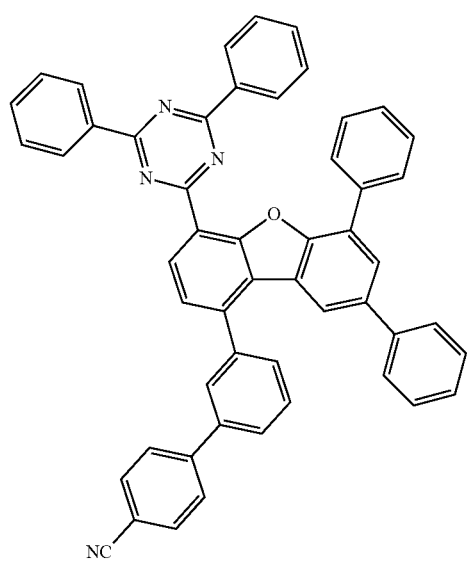
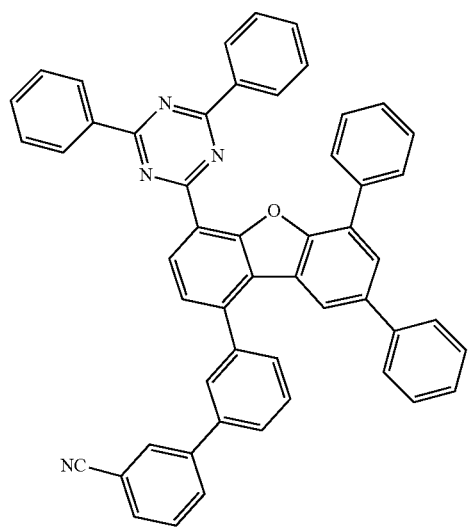
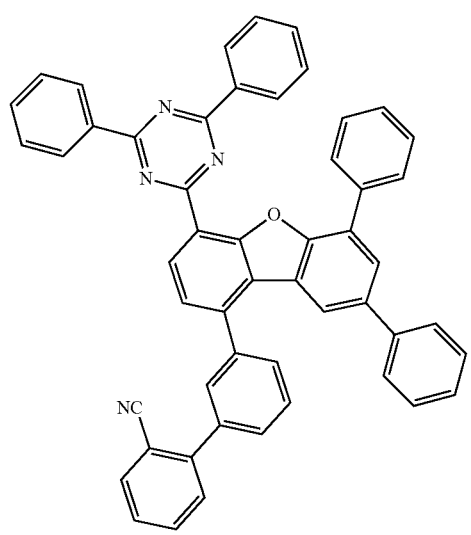
78
-continued
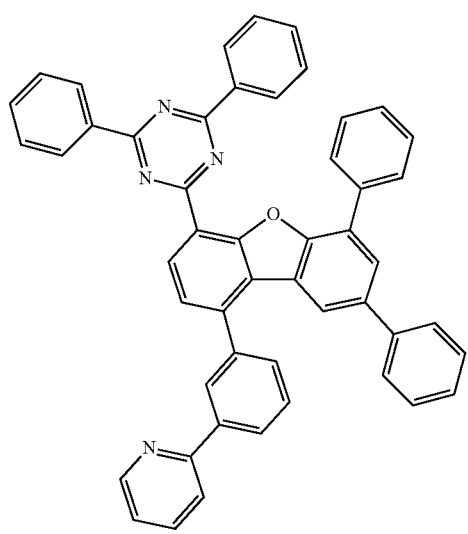
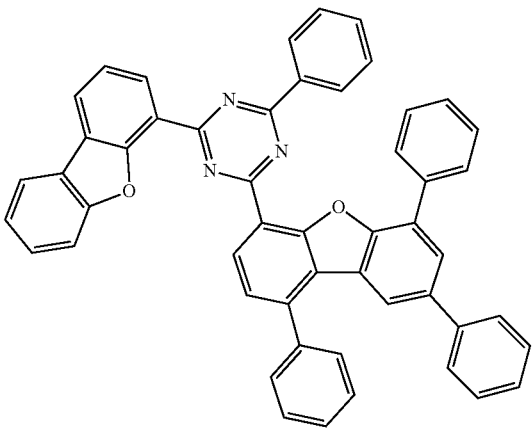
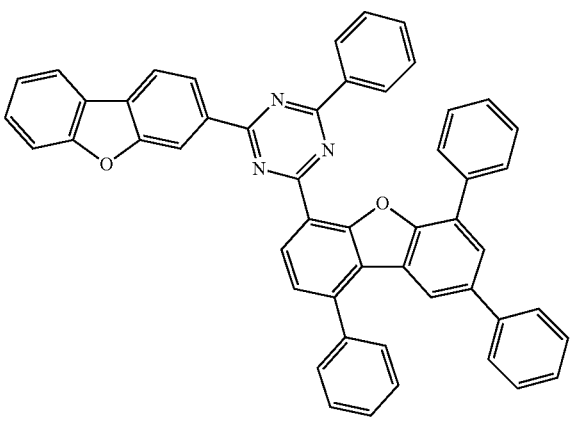

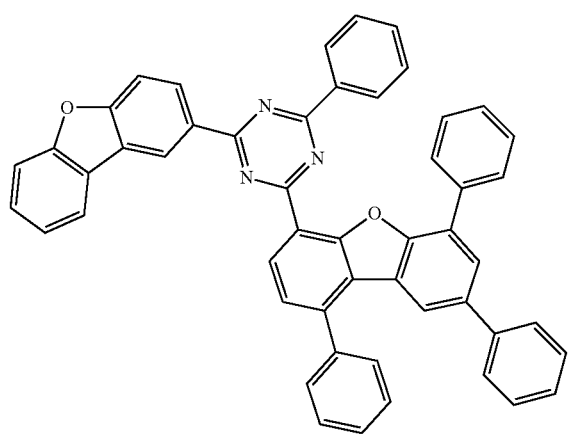
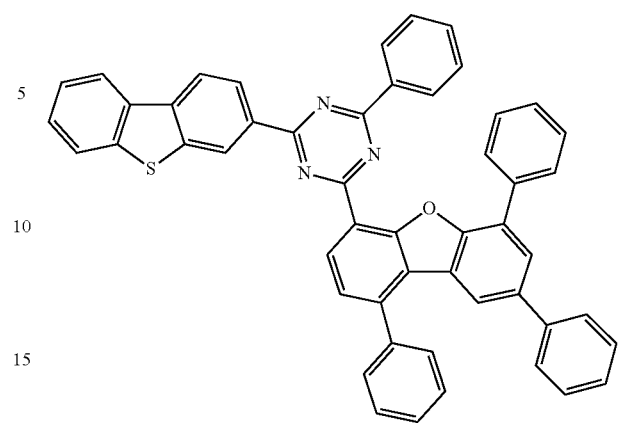
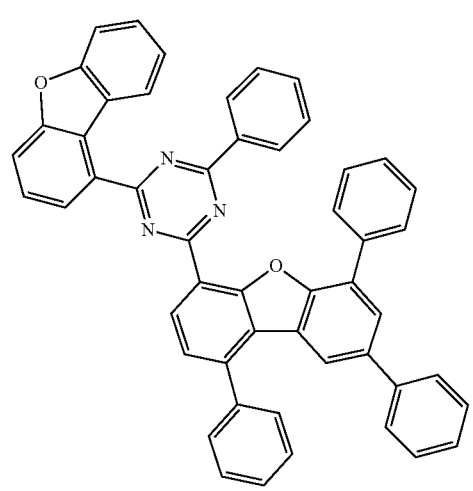
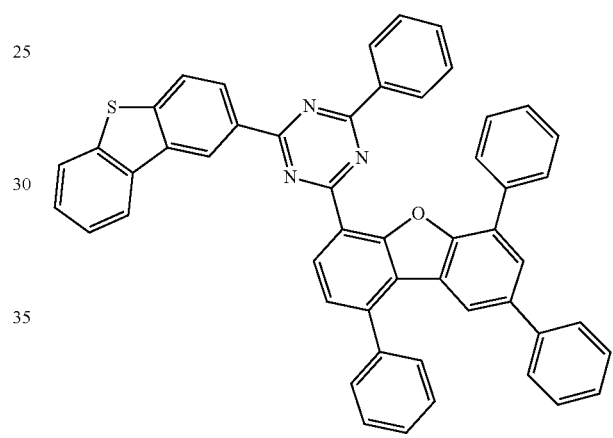
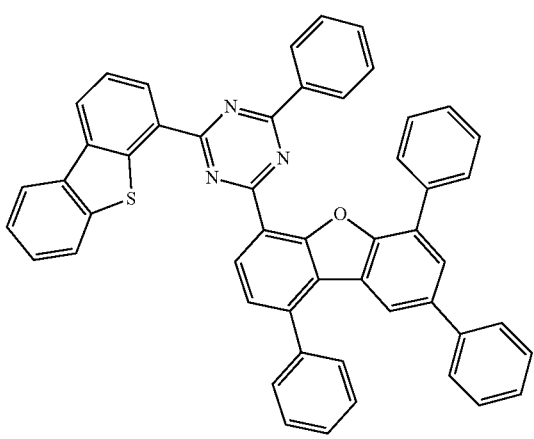
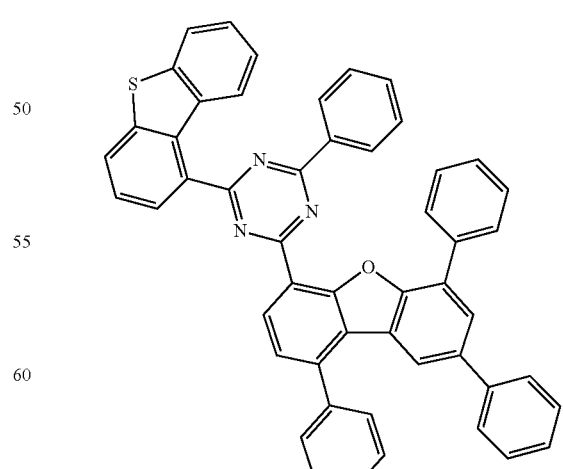

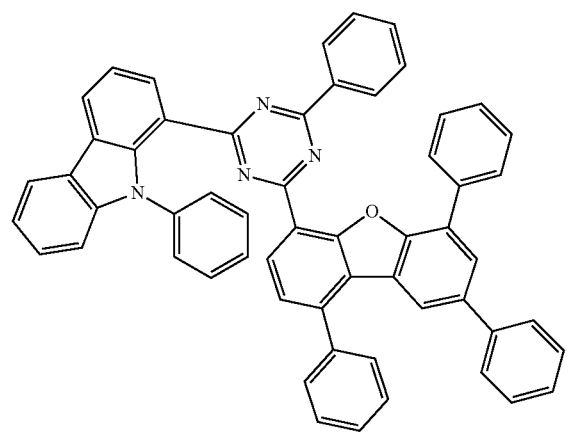
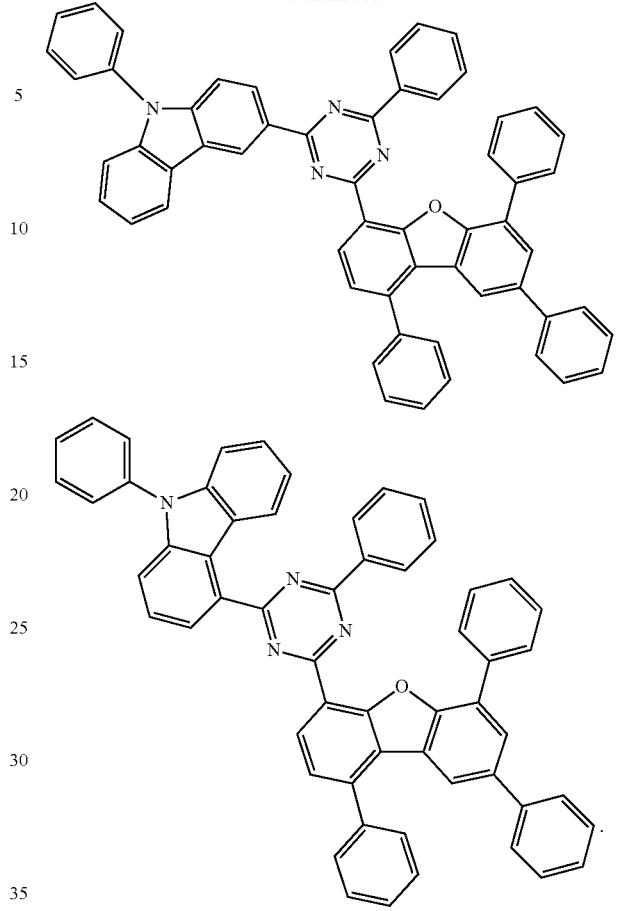
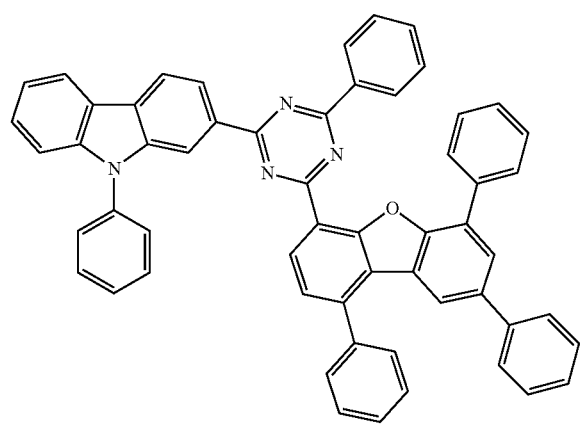
6. An organic light emitting device comprising:
a first electrode;
a second electrode provided opposite to the first electrode; and
one, two or more organic material layers provided between the first electrode and the second electrode,
wherein one or more layers of the organic material layers include the heterocyclic compound of claim 1.
* * * * *